(12) United States Patent
Hayashi et al.

(10) Patent No.: US 9,139,514 B2
(45) Date of Patent: Sep. 22, 2015

(54) PROCESS FOR PRODUCING OSELTAMIVIR PHOSPHATE AND INTERMEDIATE COMPOUND

(71) Applicant: Sumitomo Chemical Company, Ltd., Tokyo (JP)

(72) Inventors: Yujiro Hayashi, Tokyo (JP); Hayato Ishikawa, Tokyo (JP)

(73) Assignee: Sumitomo Chemical Company, Ltd., Tokyo (JP)

( * ) Notice: Subject to any disclaimer, the term of this patent is extended or adjusted under 35 U.S.C. 154(b) by 260 days.

(21) Appl. No.: 13/933,551

(22) Filed: Jul. 2, 2013

(65) Prior Publication Data

US 2013/0296600 A1 Nov. 7, 2013

Related U.S. Application Data

(62) Division of application No. 12/995,059, filed as application No. PCT/JP2009/059789 on May 28, 2009, now Pat. No. 8,501,980.

(30) Foreign Application Priority Data

May 30, 2008 (JP) .................................. 2008-143226
Dec. 5, 2008 (JP) .................................. 2008-311543

(51) Int. Cl.

| C07C 231/08 | (2006.01) |
|---|---|
| C07C 231/10 | (2006.01) |
| C07C 231/12 | (2006.01) |
| C07C 233/52 | (2006.01) |
| C07C 231/14 | (2006.01) |
| C07C 47/198 | (2006.01) |
| C07C 205/55 | (2006.01) |
| C07C 233/91 | (2006.01) |
| C07C 247/22 | (2006.01) |
| C07C 323/53 | (2006.01) |
| C07C 323/58 | (2006.01) |
| C07C 323/59 | (2006.01) |
| C07C 323/60 | (2006.01) |
| C07C 209/48 | (2006.01) |
| C07C 201/12 | (2006.01) |
| C07C 227/04 | (2006.01) |
| C07C 319/18 | (2006.01) |
| C07C 319/20 | (2006.01) |
| C07C 239/18 | (2006.01) |
| C07C 239/20 | (2006.01) |

(52) U.S. Cl.
CPC ............. *C07C 231/14* (2013.01); *C07C 47/198* (2013.01); *C07C 201/12* (2013.01); *C07C 205/55* (2013.01); *C07C 209/48* (2013.01); *C07C 227/04* (2013.01); *C07C 231/08* (2013.01); *C07C 231/10* (2013.01); *C07C 231/12* (2013.01); *C07C 233/52* (2013.01); *C07C 233/91* (2013.01); *C07C 239/18* (2013.01); *C07C 239/20* (2013.01); *C07C 247/22* (2013.01); *C07C 319/18* (2013.01); *C07C 319/20* (2013.01); *C07C 323/53* (2013.01); *C07C 323/58* (2013.01); *C07C 323/59* (2013.01); *C07C 323/60* (2013.01); *C07C 2101/14* (2013.01); *C07C 2101/16* (2013.01)

(58) Field of Classification Search
CPC .. C07C 231/08; C07C 231/12; C07C 231/10; C07C 231/14; C07C 233/52
See application file for complete search history.

(56) References Cited

PUBLICATIONS

Ishikawa et al. Angew Chem. Int. Ed. 2009, 48, 1304-1307.*

* cited by examiner

*Primary Examiner* — Matthew Coughlin
(74) *Attorney, Agent, or Firm* — Dilworth & Barrese, LLP

(57) ABSTRACT

Disclosed are a process suited to large scale synthesis with high yield for producing oseltamivir phosphate, in which a preparation of oseltamivir phosphate which is highly safe as a pharmaceutical product can be produced, and an intermediate compound for producing oseltamivir phosphate. In this production process, an intermediate compound represented by general formula (V) is synthesized by employing Michael reaction/Michael reaction/Horner-Wadsworth-Emmons reaction, and oseltamivir phosphate is produced by converting the substituent groups in this intermediate compound.

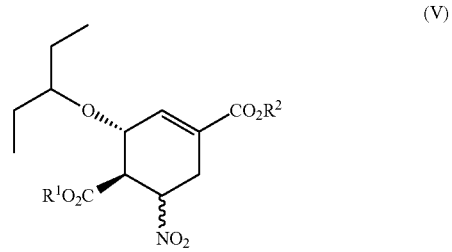

(V)

2 Claims, No Drawings

PROCESS FOR PRODUCING OSELTAMIVIR PHOSPHATE AND INTERMEDIATE COMPOUND

TECHNICAL FIELD

The present invention relates to a process for producing oseltamivir phosphate and an intermediate compound.

BACKGROUND ART

Influenza is an acute infectious disease caused by an influenza virus, and has been known to allow global pandemic threats to emerge every year. Influenza viruses infect host cells by incorporation of hemagglutinin that is a protein present on the surface of virus particles into host cells via binding to a glycoprotein on the surface of the host cells, followed by proliferation in the host cells, and subsequently the viruses are secreted out of the cells and infect another host cells.

When thus proliferated influenza viruses in host cells are secreted out of the cells, glycoproteins present on the cell surface of the host cells form complexes with hemagglutinin present on the surface of the virus particles. For releasing the virus particles from the host cells to infect other host cells, it is necessary to cleave binding between the glycoprotein and hemagglutinin, and the cleavage of this binding is carried out by neuraminidase present on the surface of the virus particles.

Oseltamivir phosphate has been known to inhibit the activity of neuraminidase, and has been used as a specific medicine for influenza. Oseltamivir phosphate has been conventionally synthesized by way of semisynthesis using shikimic acid, which is a natural substance, as a starting material (for example, see Nonpatent Document 1). However, stable supply may be difficult since the starting material is a natural substance, and thus development of a synthetic method carried out by total synthesis without using a natural substance has been demanded.

In this regard, as an intermediate for synthesizing oseltamivir phosphate by total synthesis, Patent Document 1 discloses an intermediate for producing oseltamivir phosphate, i.e., a precursor to oseltamivir phosphate, synthesized by employing a Diels-Alder reaction. In addition, Nonpatent Document 1 discloses a process for synthesizing oseltamivir phosphate using as a starting material a shikimic acid which is isolated from a natural product. Nonpatent Document 2 discloses a process for synthesizing oseltamivir phosphate starting from a dissymmetric asymmetric Diels-Alder reaction in which oxazaborolidine is utilized as an asymmetric catalyst. Nonpatent Document 3 discloses a process for synthesizing oseltamivir phosphate in which an asymmetric ring-opening reaction of a mesoaziridine ring catalyzed by an yttrium catalyst is used. Nonpatent Document 4 discloses a process for synthesizing oseltamivir phosphate starting from a dissymmetric asymmetric Diels-Alder reaction of a dihydropyridine derivative derived from pyridine. Furthermore, Nonpatent Document 5 discloses a process for synthesizing oseltamivir phosphate starting from asymmetric alkylation of an allylic position using palladium as a catalyst.

Patent Document 1: Japanese Unexamined Patent Application, Publication No. 2008-081489
Nonpatent Document 1: J. Am. Chem. Soc., vol. 119, p. 681 (1997)
Nonpatent Document 2: J. Am. Chem. Soc., vol. 128, p. 6310 (2006)
Nonpatent Document 3: J. Am. Chem. Soc., vol. 128, p. 6312 (2006)
Nonpatent Document 4: Angew. Chem. vol. 119, p. 5836 (2007); Angew. Chem. Int. Ed. vol. 46, p. 5734 (2007)
Nonpatent Document 5: Angew. Chem. vol. 120, p. 3819 (2008); Angew. Chem. Int. Ed. vol. 47, p. 3759 (2008)

DISCLOSURE OF THE INVENTION

Problems to be Solved by the Invention

However, when oseltamivir phosphate is synthesized by the process disclosed in Patent Document 1 and Nonpatent Documents 2 to 5, a large number of reactions are required, and thus the reaction yield as a whole may be decreased. In addition, any of the processes use an asymmetric catalyst; however, these have been practically problematic in terms of use of an expensive asymmetric catalyst, and necessity of the reaction to be carried out in an anhydrous and inert atmosphere. Therefore, it is impossible to employ the aforementioned process for synthesizing oseltamivir phosphate for industrially producing oseltamivir phosphate on a large scale. Additionally, since a large number of metal elements are used for reaction catalysts in these processes for synthesizing oseltamivir phosphate, there exists a problem of failure in use of the resulting oseltamivir phosphate preparation as a pharmaceutical product with a safe conscience.

The present invention was made in view of the foregoing problems, and an object of the invention is to provide a process for producing oseltamivir phosphate, and an intermediate compound for producing oseltamivir phosphate capable of producing an oseltamivir phosphate preparation that is highly safe as a pharmaceutical product, and being suitable for synthesis on a large scale with high yield.

Means for Solving the Problems

The present inventors thoroughly investigated in order to solve the foregoing problems. As a result, it was found that the problems can be solved by employing Michael reaction/Michael reaction/Horner-Wadsworth-Emmons reactions to prepare an intermediate compound having a basic skeleton of oseltamivir phosphate, and converting the substituent of the intermediate compound. Consequently, the present invention was completed. Specifically, the present invention provides as in the following.

A first aspect of the invention provides a process for producing oseltamivir phosphate including any one, or at least two sequential steps of the following step (1-1) to step (1-8):

(1-1) a step of subjecting a compound represented by the following general formula (I) and a compound represented by the following general formula (II) to a Michael reaction, and subjecting thus obtained compound and a compound represented by the following general formula (III) or the general formula (IV) to a Michael reaction and a Horner-Wadsworth-Emmons reaction to obtain a compound represented by the following general formula (V):

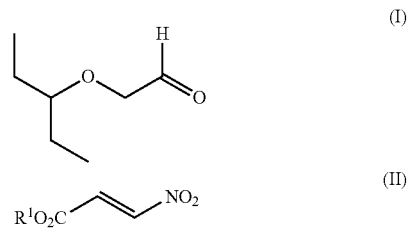

-continued

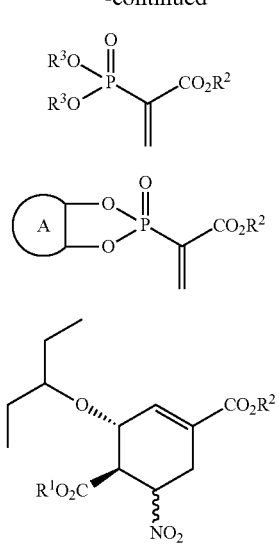

in the general formulae (II) to (V), $R^1$ represents a protecting group of a carboxyl group; $R^2$ represents an alkyl group, an aryl group, a heteroaryl group, a cycloalkyl group, or a heterocycloalkyl group which may have a substituent; $R^3$ each independently represents an alkyl group, an aryl group, a heteroaryl group, a cycloalkyl group, or a heterocycloalkyl group which may have a substituent, and may form a ring structure by linking with each other; and A represents an arylene group, a heteroarylene group, a cycloalkylene group, or a heterocycloalkylene group which may have a substituent;

(1-2) a step of subjecting the compound represented by the above general formula (V) and a thiol compound to a Michael reaction to obtain a compound represented by the following general formula (VI):

(VI)

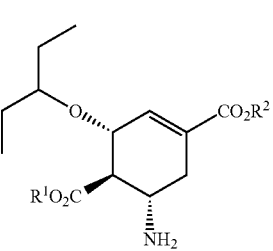

in the general formula (VI), $R^1$ and $R^2$ are as defined above; and $R^4$ represents an aryl group, a heteroaryl group, a cycloalkyl group, a heterocycloalkyl group, a cycloalkenyl group, a heterocycloalkenyl group, an alkyl group, an alkenyl group, or an alkynyl group which may have a substituent;

(1-3) a step of reducing the compound represented by the above general formula (VI), and subjecting to a reverse Michael reaction to obtain a compound represented by the following general formula (VII):

(VII)

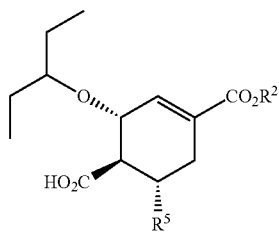

in the general formula (VII), $R^1$ and $R^2$ are as defined above;

(1-4) a step of protecting an amino group of the compound represented by the above general formula (VII) and deprotecting a carboxyl group to obtain a compound represented by the following general formula (VIII):

(VIII)

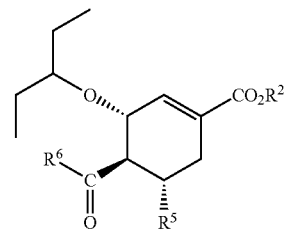

in the general formula (VIII), $R^2$ is as defined above; and $R^5$ represents a group in which a protecting group is bound to an amino group;

(1-5) a step of halogenating a carboxyl group of the compound represented by the above general formula (VIII) to obtain a compound represented by the following general formula (IX):

(IX)

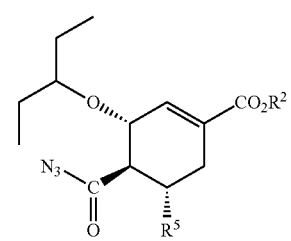

in the general formula (IX), $R^2$ and $R^5$ are as defined above; and $R^6$ represents a halogen atom;

(1-6) a step of allowing the compound represented by the above general formula (IX) to react with an azide to obtain a compound represented by the following general formula (X):

(X)

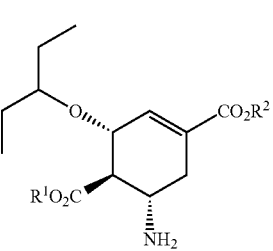

in the general formula (X), $R^2$ and $R^5$ are as defined above;

(1-7) a step of subjecting the compound represented by the above general formula (X) to a Curtius rearrangement reaction to obtain a compound represented by the following general formula (XI):

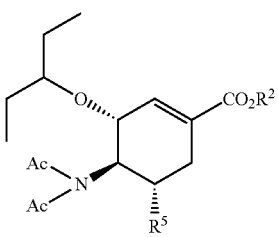

(XI)

in the general formula (XI), R² and R⁵ are as defined above; and (1-8) deacetylating the compound represented by the above general formula (XI) and deprotecting an amino group to obtain a compound represented by the following general formula (XII):

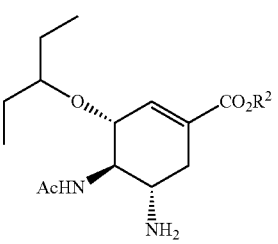

(XII)

in the general formula (XII), R² is as defined above.

A second aspect of the invention provides a process for producing oseltamivir phosphate including any one, or at least two sequential steps of the following step (2-1) to step (2-9):

(2-1) a step of subjecting a compound represented by the following general formula (I) and a compound represented by the following general formula (II) to a Michael reaction, and subjecting thus obtained compound and a compound represented by the following general formula (III) or the general formula (IV) to a Michael reaction and a Horner-Wadsworth-Emmons reaction to obtain a compound represented by the following general formula (V):

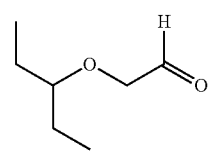

(I)

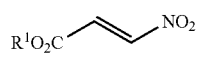

(II)

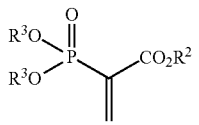

(III)

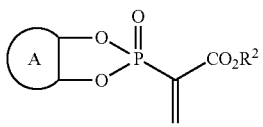

(IV)

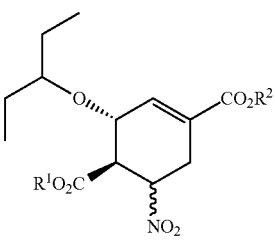

(V)

in the general formulae (II) to (V), R¹ represents a protecting group of a carboxyl group; R² represents an alkyl group, an aryl group, a heteroaryl group, a cycloalkyl group, or a heterocycloalkyl group which may have a substituent; R² each independently represents an alkyl group, an aryl group, a heteroaryl group, a cycloalkyl group, or a heterocycloalkyl group which may have a substituent, and may form a ring structure by linking with each other; and A represents an arylene group, a heteroarylene group, a cycloalkylene group, or a heterocycloalkylene group which may have a substituent;

(2-2) a step of subjecting the compound represented by the above general formula (V) and a thiol compound to a Michael reaction to obtain a compound represented by the following general formula (VI):

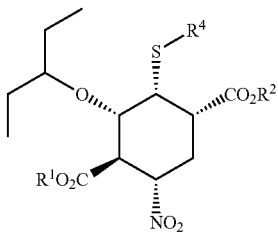

(VI)

in the general formula (VI), R¹ and R² are as defined above; and R⁴ represents an aryl group, a heteroaryl group, a cycloalkyl group, a heterocycloalkyl group, a cycloalkenyl group, a heterocycloalkenyl group, an alkyl group, an alkenyl group, or an alkynyl group which may have a substituent;

(2-3) a step of deprotecting a carboxyl group of the compound represented by the above general formula (VI) to obtain a compound represented by the following general formula (XIII):

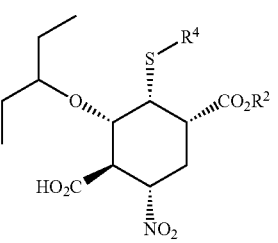

(XIII)

in the general formula (XIII), R² and R⁴ are as defined above;

(2-4) a step of halogenating a carboxyl group of the compound represented by the above general formula (XIII) to obtain a compound represented by the following general formula (XIV):

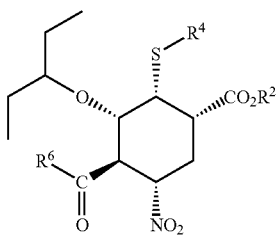

(XIV)

in the general formula (XIV), $R^2$ and $R^4$ are as defined above; and $R^6$ represents a halogen atom;

(2-5) a step of allowing the compound represented by the above general formula (XIV) to react with an azide to obtain a compound represented by the following general formula (XV):

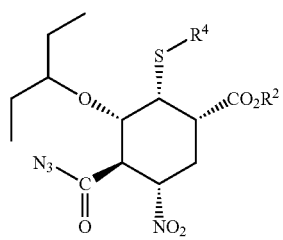

(XV)

in the general formula (XV), $R^2$ and $R^4$ are as defined above;

(2-6) a step of subjecting the compound represented by the above general formula (XV) to a Curtius rearrangement reaction to obtain a compound represented by the following general formula (XVI):

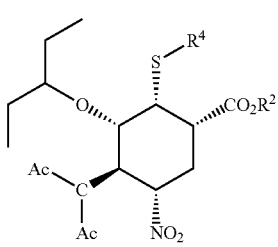

(XVI)

in the general formula (XVI), $R^2$ and $R^4$ are as defined above;

(2-7) a step of deacetylating the compound represented by the above general formula (XVI) to obtain a compound represented by the following general formula (XVII):

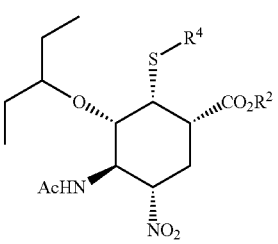

(XVII)

in the general formula (XVII), $R^2$ and $R^4$ are as defined above;

(2-8) reducing the compound represented by the above general formula (XVII) to obtain a compound represented by the following general formula (XVIII):

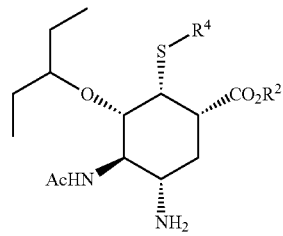

(XVIII)

in the general formula (XVIII), $R^2$ and $R^4$ are as defined above; and (2-9) a step of subjecting the compound represented by the above general formula (XVIII) to a reverse Michael reaction to obtain a compound represented by the following general formula (XII):

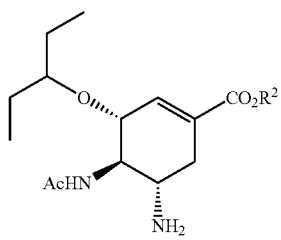

(XII)

in the general formula (XII), is as defined above.

A third aspect of the invention provides an intermediate compound for producing oseltamivir phosphate represented by the following general formula (A):

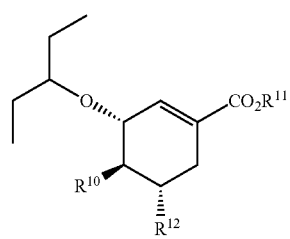

(A)

in the general formula (A), $R^{10}$ represents —$NAc_2$, a carboxyl group, or a group in which a protecting group is bound to a carboxyl group; $R^{11}$ represents an alkyl group, an aryl group, a heteroaryl group, a cycloalkyl group, or a heterocycloalkyl group which may have a substituent; and $R^{12}$ represents a group in which a protecting group is bound to an amino group, an amino group, a hydroxyamino group, or an alkoxyamino group.

A fourth aspect of the invention provides an intermediate compound for producing oseltamivir phosphate represented by the following general formula (A'):

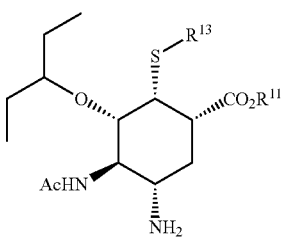

(A')

in the general formula (A'), $R^{11}$ represents an alkyl group, an aryl group, a heteroaryl group, a cycloalkyl group, or a heterocycloalkyl group which may have a substituent; and $R^{13}$ represents an aryl group, a heteroaryl group, a cycloalkyl group, a heterocycloalkyl group, a cycloalkenyl group, a heterocycloalkenyl group, an alkyl group, an alkenyl group, or an alkynyl group which may have a substituent.

A fifth aspect of the invention provides an intermediate compound for producing oseltamivir phosphate represented by the following general formula (B):

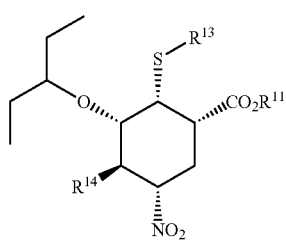

(B)

in the general formula (B), $R^{11}$ represents an alkyl group, an aryl group, a heteroaryl group, a cycloalkyl group, or a heterocycloalkyl group which may have a substituent; $R^{13}$ represents an aryl group, a heteroaryl group, a cycloalkyl group, a heterocycloalkyl group, a cycloalkenyl group, a heterocycloalkenyl group, an alkyl group, an alkenyl group, or an alkynyl group which may have a substituent; and $R^{14}$ represents a carboxyl group, a group in which a protecting group is bound to a carboxyl group, a halogenated carbonyl group, —C(=O)—$N_2$, —NCO, —$NAc_2$, or —NHAc.

A sixth aspect of the invention provides an intermediate compound for producing oseltamivir phosphate represented by the following general formula (C):

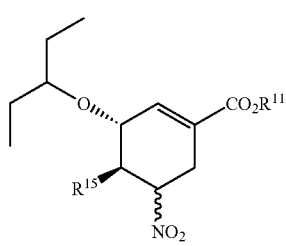

(C)

in the general formula (C), $R^{11}$ represents an alkyl group, an aryl group, a heteroaryl group, a cycloalkyl group, or a heterocycloalkyl group which may have a substituent; and $R^{15}$ represents a carboxyl group, or a group in which a protecting group is bound to a carboxyl group.

A seventh aspect of the invention provides an intermediate compound for producing oseltamivir phosphate represented by the following general formula (C'):

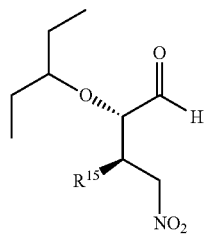

(C')

in the general formula (C'), $R^{15}$ represents a carboxyl group, or a group in which a protecting group is bound to a carboxyl group.

An eighth aspect of the invention provides an intermediate compound for producing oseltamivir phosphate represented by the following structural formula (D):

(D)

A ninth aspect of the invention provides an intermediate compound for producing oseltamivir phosphate according to any one of the third to sixth aspects in which $R^{11}$ is an ethyl group.

A tenth aspect of the invention provides an intermediate compound for producing oseltamivir phosphate according to the fourth or fifth aspect in which $R^{13}$ is a p-methylphenyl group.

Effects of the Invention

In the process for producing oseltamivir phosphate of the present invention, safety of the produced oseltamivir phosphate preparation can be sufficiently ensured since a large variety of metal elements are not used as catalysts. In addition, since an intermediate compound having a basic skeleton of oseltamivir phosphate is prepared in the initial reaction, and thereafter a substituent of the intermediate compound is converted in the process for producing oseltamivir phosphate, oseltamivir phosphate can be synthesized with a small number of reactions, and the yield as a whole can be also maintained at a high level.

PREFERRED MODE FOR CARRYING OUT THE INVENTION

Hereinafter, details of embodiments of the present invention are explained.

<Process for Producing Oseltamivir Phosphate of the First Embodiment>

The process for producing oseltamivir phosphate of the first embodiment in the present invention is explained below. It should be noted that although the following step (1-1) to step (1-8) are explained below, the method does not necessarily include all these steps. In other words, the invention falls within the scope of the present invention as long as at least one step of the following step (1-1) to step (1-8) is included.

First, in the step (1-1), a compound represented by the following general formula (I) and a compound represented by the following general formula (II) are subjected to a Michael reaction, and thus obtained compound and a compound represented by the following general formula (III) or the general formula (IV) are subjected to a Michael reaction and a Horner-Wadsworth-Emmons reaction to obtain a compound represented by the following general formula (V).

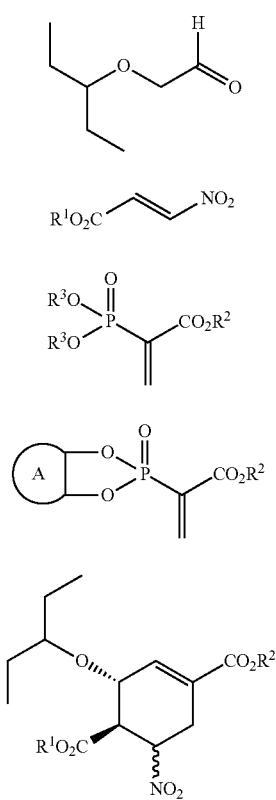

In the general formulae (II) to (V), $R^1$ represents a protecting group of a carboxyl group; $R^2$ represents an alkyl group, an aryl group, a heteroaryl group, a cycloalkyl group, or a heterocycloalkyl group which may have a substituent; $R^3$ each independently represents an alkyl group, an aryl group, a heteroaryl group, a cycloalkyl group, or a heterocycloalkyl group which may have a substituent, and may form a ring structure by linking with each other; and A represents an arylene group, a heteroarylene group, a cycloalkylene group, or a heterocycloalkylene group which may have a substituent.

In the general formulae (II) and (V), the protecting group of the carboxyl group represented by $R^1$ is exemplified by a methyl ester group, an ethyl ester group, a benzyl ester group, a tert-butyl ester group, and the like.

When the compound represented by the above general formula (I) and the compound represented by the above general formula (II) are subjected to a Michael reaction, a catalyst represented by the following general formula (E) may be used.

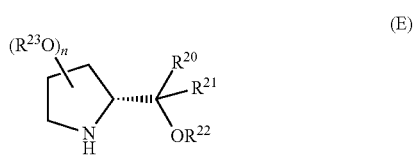

In the general formula (E), $R^{20}$ and $R^{21}$ each independently represent an aryl group, a heteroaryl group, a cycloalkyl group, a heterocycloalkyl group, a cycloalkenyl group, a heterocycloalkenyl group, an alkyl group, an alkenyl group, or an alkynyl group which may have a substituent; $R^{22}$ represents a hydrogen atom, a silyl group, or an alkyl group; and $R^{23}$ represents a protecting group of a hydroxyl group, and n represents 0 or 1.

In the above general formula (E), as a protecting group of the hydroxyl group represented by $R^{23}$, a commonly used protecting group such as an alkyl group, an acetyl group or a silyl group may be used. Moreover, when n is 1, substitution position of $OR^{23}$ group may be either 3-position or 4-position.

Herein, "aryl group" which may be used either alone or as a part of other group represents an aromatic hydrocarbon group unless otherwise stated particularly, and at least two rings may be condensed. Although the carbon number of the aryl group is not particularly limited, the carbon number is preferably 5 or greater and 14 or less, and more preferably 6 or greater and 10 or less. Examples of the aryl group include a phenyl group, an indenyl group, a naphthyl group, a phenanthryl group, an anthryl group, and the like.

This aryl group may be unsubstituted, or one or more hydrogen atoms thereof may be substituted with a substituent. The substituent may include an alkyl group, an alkoxy group, an alkoxyalkyl group, an alkoxycarbonyl group, an alkoxycarbonylalkyl group, an acyl group, an acylalkyl group, an alkylthio group, an alkylenedioxy group, a halogen atom, an amino group, a nitro group, a cyano group, a thiol group, a hydroxyl group, and the like.

Herein, "heteroaryl group" which may be used either alone or as a part of other group represents a group having substitution of at least one carbon atom on the ring of the aryl group with a hetero atom, unless otherwise stated particularly. The hetero atom may include an oxygen atom, a nitrogen atom, and a sulfur atom. Examples of the heteroaryl group include a pyridyl group, a pyrazinyl group, a pyrimidinyl group, a pyridazinyl group, a pyrrolyl group, an imidazolyl group, a pyrazolyl group, a triazolyl group, a triazinyl group, a tetrazolyl group, an oxazolyl group, an indolizinyl group, an indolyl group, an isoindolyl group, an indazolyl group, a purinyl group, a quinolizinyl group, an isoquinolyl group, a quinolyl group, a phthalazinyl group, a naphthyridinylgroup, a quinoxalinyl group, an oxadiazolyl group, a triazolyl group, a thiadiazolyl group, a benzimidazolyl group, a furyl group, a thienyl group, and the like.

The heteroaryl group may be unsubstituted, or one or more hydrogen atoms thereof may be substituted with a substituent. As the substituent, the groups described above in connection with the substituent of the aryl group may be exemplified.

Herein, "cycloalkyl group" which may be used either alone or as a part of other group represents a nonaromatic saturated cyclic hydrocarbon group unless otherwise stated particularly. Although the carbon number of the cycloalkyl group is not particularly limited, the carbon number is preferably 3 or greater and 10 or less, and more preferably 3 or greater and 6 or less. Examples of the cycloalkyl group include a cyclopropyl group, a cyclobutyl group, a cyclopentyl group, a cyclohexyl group, a cycloheptyl group, and the like.

The cycloalkyl group may be unsubstituted, or one or more hydrogen atoms thereof may be substituted with a substituent. As the substituent, an alkyl group, an alkoxy group, an alkoxyalkyl group, an alkoxycarbonyl group, an alkoxycarbonylalkyl group, an acyl group, an acylalkyl group, an alkylthio group, a halogen atom, an amino group, a nitro group, a cyano group, a thiol group, a hydroxyl group, and the like may be exemplified.

Herein, "heterocycloalkyl group" which may be used either alone or as a part of other group represents a group having substitution of at least one carbon atom on the ring of the cycloalkyl group with a hetero atom, unless otherwise stated particularly. The hetero atom may include an oxygen atom, a nitrogen atom, and a sulfur atom. Examples of the heterocycloalkyl group include a tetrahydrofuryl group, a morpholinyl group, a piperazinyl group, a piperidyl group, a pyrrolidinyl group, and the like.

The heterocycloalkyl group may be unsubstituted, or one or more hydrogen atoms thereof may be substituted with a substituent. As the substituent, the groups described above in connection with the substituent of the cycloalkyl group may be exemplified.

Herein, "cycloalkenyl group" which may be used either alone or as a part of other group represents a nonaromatic unsaturated cyclic hydrocarbon group unless otherwise stated particularly. The ring may have one, or at least two unsaturated linkage(s). Although the carbon number of the cycloalkenyl group is not particularly limited, the carbon number is preferably 3 or greater and 10 or less, and more preferably 3 or greater and 6 or less. Examples of the cycloalkenyl group include a cyclopropenyl group, a cyclobutenyl group, a cyclopentenyl group, a cyclohexenyl group, a cycloheptenyl group, and the like.

The cycloalkenyl group may be unsubstituted, or one or more hydrogen atoms thereof may be substituted with a substituent. As the substituent, the groups described above in connection with the substituent of the cycloalkyl group may be exemplified.

Herein, "heterocycloalkenyl group" which may be used either alone or as a part of other group represents a group having substitution of at least one carbon atom on the ring of the cycloalkenyl group with a hetero atom, unless otherwise stated particularly. The hetero atom may include an oxygen atom, a nitrogen atom, and a sulfur atom. Examples of the heterocycloalkenyl group include a dihydrofuryl group, an imidazolyl group, a pyrrolinyl group, a pyrazolinyl group, and the like.

The heterocycloalkenyl group may be unsubstituted, or one or more hydrogen atoms thereof may be substituted with a substituent. As the substituent, the groups described above in connection with the substituent of the cycloalkyl group may be exemplified.

Herein, "alkyl group" which may be used either alone or as a part of other group may be either linear or branched, unless otherwise stated particularly. Although the carbon number of the alkyl group is not particularly limited, the carbon number is preferably 1 or greater and 20 or less, and more preferably 1 or greater and 6 or less. Examples of the alkyl group include a methyl group, an ethyl group, a n-propyl group, an isopropyl group, a n-butyl group, an isobutyl group, a sec-butyl group, a t-butyl group, a n-pentyl group, an isopentyl group, a n-hexyl group, a n-pentyl group, and the like.

The alkyl group may be unsubstituted, or one or more hydrogen atoms thereof may be substituted with a substituent. As the substituent, alkoxy group, acyl group, a halogen atom, an amino group, a nitro group, a cyano group, a thiol group, a hydroxyl group, and the like may be exemplified.

Herein, "alkenyl group" which may be used either alone or as a part of other group may be either linear or branched, unless otherwise stated particularly. Although the carbon number of the alkenyl group is not particularly limited, the carbon number is preferably 2 or greater and 20 or less, and more preferably 2 or greater and 6 or less. Examples of the alkenyl group include a vinyl group, a 1-propenyl group, an allyl group, an isopropenyl, a 1-butenyl group, an isobutenyl group, and the like.

The alkenyl group may be unsubstituted, or one or more hydrogen atoms thereof may be substituted with a substituent. As the substituent, the groups described above in connection with the substituent of the alkyl group may be exemplified.

Herein, "alkynyl group" which may be used either alone or as a part of other group may be either linear or branched, unless otherwise stated particularly. Although the carbon number of the alkynyl group is not particularly limited, the carbon number is preferably 2 or greater and 20 or less, and more preferably 2 or greater and 6 or less. Examples of the alkynyl group include an ethynyl group, a 1-propynyl group, a 2-propynyl group, an isopropynyl group, a 1-butynyl group, an isobutynyl group, and the like.

The alkynyl group may be unsubstituted, or one or more hydrogen atoms thereof may be substituted with a substituent. As the substituent, the groups described above in connection with the substituent of the alkyl group may be exemplified.

Herein, "silyl group" means a group represented by $H_3Si$—, or a group having substitution of at least one hydrogen atom of this group with an alkyl group, an aryl group or the like. Examples of the silyl group include a trimethylsilyl (TMS) group, a triethylsilyl (TES) group, a t-butyldimethylsilyl (TBS) group, a triisopropylsilyl (TIPS) group, a t-butyldiphenylsilyl (TBDPS) group, and the like.

Next, in the step (1-2), a compound represented by the following general formula (VI) is obtained by subjecting the compound represented by the above general formula (V) and a thiol compound to a Michael reaction.

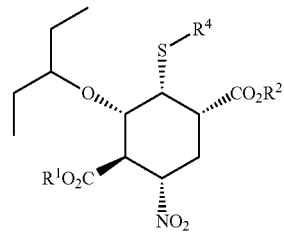

(VI)

In the general formula (VI), $R^1$ and $R^2$ are as defined above; and $R^4$ represents an aryl group, a heteroaryl group, a cycloalkyl group, a heterocycloalkyl group, a cycloalkenyl group, a heterocycloalkenyl group, an alkyl group, an alkenyl group, or an alkynyl group which may have a substituent.

The thiol compound allowed to react with the compound represented by the above general formula (V) may include p-toluenethiol, benzenethiol, naphthylthiol, ethanethiol, dodecylthiol, and the like.

Next, in the step (1-3), a compound represented by the following general formula (VII) is obtained by reducing the compound represented by the above general formula (VI), and subjecting to a reverse Michael reaction.

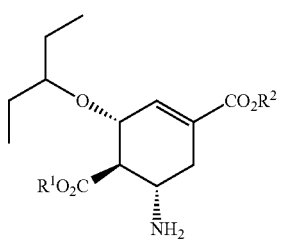

(VII)

In the general formula (VII), $R^1$ and $R^2$ are as defined above.

Next, in the step (1-4), a compound represented by the following general formula (VIII) is obtained by carrying out protection of the amino group of the compound represented by the above general formula (VII), and deprotection of the carboxyl group.

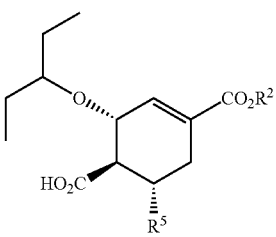

(VIII)

In the general formula (VIII), $R^2$ is as defined above; and $R^5$ represents a group in which a protecting group is bound to an amino group.

In the above the general formula (VIII), the protecting group of the amino group may include a tert-butoxycarbonyl group, a benzyloxycarbonyl group, a 9-fluorenylmethyloxycarbonyl group, a 2,2,2-trichloroethoxycarbonyl group, an allyloxycarbonyl group, a phthaloyl group, a p-toluenesulfonyl group, a p-nitrobenzenesulfonyl group, and the like.

Next, in the step (1-5), a compound represented by the following general formula (IX) is obtained by halogenating the carboxyl group of the compound represented by the above general formula (VIII).

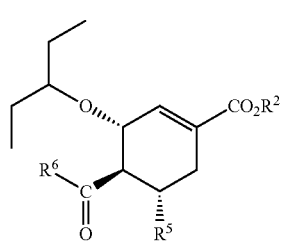

(IX)

In the general formula (IX), $R^2$ and $R^5$ are as defined above; and $R^6$ represents a halogen atom.

Next, in the step (1-6), a compound represented by the following general formula (X) is obtained by allowing the compound represented by the above general formula (IX) to react with an azide.

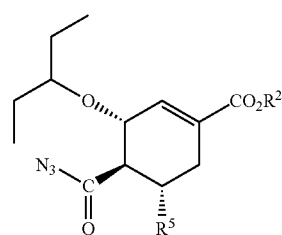

(X)

In the general formula (X), $R^2$ and $R^5$ are as defined above.

The azide allowed to react with the compound represented by the above general formula (IX) may include sodium azide, lithium azide, trimethylsilyl azide, and the like.

Next, in the step (1-7), a compound represented by the following general formula (XI) is obtained by subjecting the compound represented by the above general formula (X) to a Curtius rearrangement reaction.

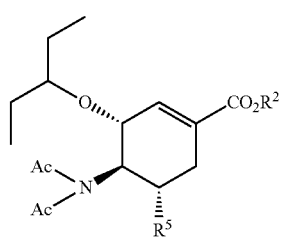

(XI)

In the general formula (XI), $R^2$ and $R^5$ are as defined above.

Next, in the step (1-8), a compound represented by the following general formula (XII) is obtained by carrying out deacetylation, and deprotection of the amino group of the compound represented by the above general formula (XI).

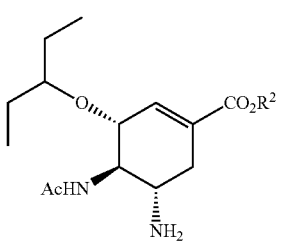

(XII)

In the general formula (XII), $R^2$ is as defined above.

In the production process according to the first embodiment, the step (1-1) can be carried out in one pot. Thus, when practiced on an industrial scale, the production process can be simplified. Moreover, since the compound represented by the above general formula (V) having a basic skeleton of oseltamivir phosphate can be synthesized in this reaction, the intended oseltamivir phosphate can be synthesized by merely converting the substituent, and the like in the subsequent reaction. Thus, the number of reactions in the entirety of the process for producing oseltamivir phosphate can be decreased.

<Process for Producing Oseltamivir Phosphate of Second Embodiment>

Hereinafter, the process for producing oseltamivir phosphate of the second embodiment in the present invention is explained. It should be noted that the following step (2-1) to step (2-9) are explained below; however, all these steps may not be necessarily included. In other words, the process is involved in the scope of the present invention as long as at least one of the following step (2-1) to step (2-9) is included.

First, in the step (2-1) and the step (2-2), the compound represented by the above general formula (VI) is obtained similarly to the aforementioned step (1-1) and the step (1-2).

Next, in the step (2-3), a compound represented by the following general formula (XIII) is obtained by deprotecting a carboxyl group of the compound represented by the above general formula (VI).

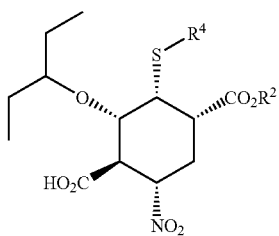

(XIII)

In the general formula (XIII), $R^2$ and $R^4$ are as defined above.

Next, in the step (2-4), a compound represented by the following general formula (XIV) is obtained by halogenating the carboxyl group of the compound represented by the above general formula (XIII).

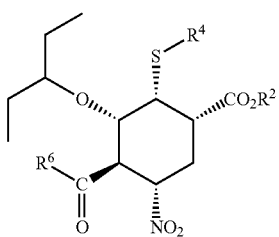

(XIV)

In the general formula (XIV), $R^2$ and $R^4$ are as defined above; and $R^6$ represents a halogen atom.

Next, in the step (2-5), a compound represented by the following general formula (XV) is obtained by allowing the compound represented by the above general formula (XIV) to react with an azide.

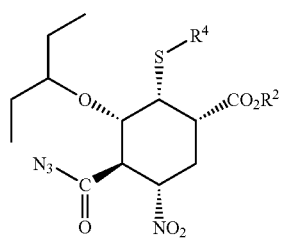

(XV)

In the general formula (XV), $R^2$ and $R^4$ are as defined above.

The azide allowed to react with the compound represented by the above general formula (XIV) may include sodium azide, lithium azide, trimethylsilyl azide, and the like.

Next, in the step (2-6), a compound represented by the following general formula (XVI) is obtained by subjecting the compound represented by the above general formula (XV) to a Curtius rearrangement reaction.

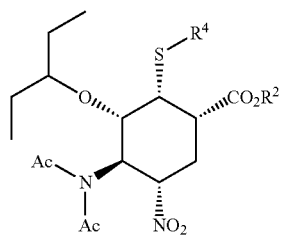

(XVI)

In the general formula (XVI), $R^2$ and $R^4$ are as defined above.

Next, in the step (2-7), a compound represented by the following general formula (XVII) is obtained by deacetylating the compound represented by the above general formula (XVI).

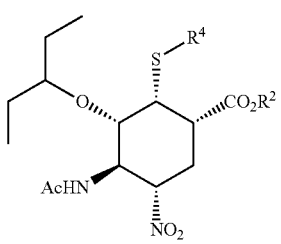

(XVII)

In the general formula (XVII), $R^2$ and $R^4$ are as defined above.

Next, in the step (2-8), a compound represented by the following general formula (XVIII) is obtained by reducing the compound represented the above general formula (XVII).

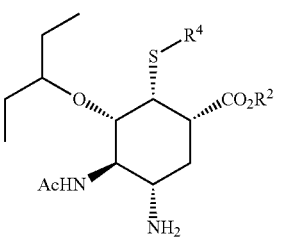

(XVIII)

In the general formula (XVIII), $R^2$ and $R^4$ are as defined above.

Next, in the step (2-9), the compound represented by the above general formula (XII) is obtained by subjecting the compound represented by the above general formula (XVIII) to a reverse Michael reaction.

In the production process according to the second embodiment, the step (2-1) to step (2-2), step (2-3) to step (2-5), and step (2-6) to step (2-9) can be carried out in one pot. Thus, when practiced on an industrial scale, the production process can be simplified, and also the yield as a whole can be improved.

<Intermediate Compound of Oseltamivir Phosphate>

The intermediate compound for producing oseltamivir phosphate of the present invention is exemplified by the compounds represented by the following general formulae (A) to (C), (A') and (C'), and the chemical formula (D).

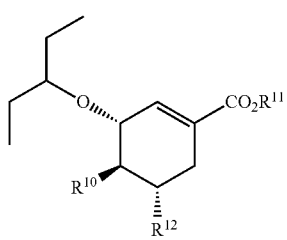

(A)

In the general formula (A), $R^{10}$ represents —$NAc_2$, a carboxyl group, or a group in which a protecting group is bound to a carboxyl group; $R^{11}$ represents an alkyl group, an aryl group, a heteroaryl group, a cycloalkyl group, or a heterocycloalkyl group which may have a substituent; and $R^{12}$ represents a group in which a protecting group is bound to an amino group, an amino group, a hydroxyamino group, or an alkoxyamino group.

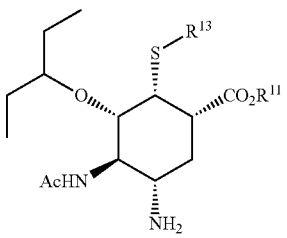

(A')

In the general formula (A'), $R^{11}$ represents an alkyl group, an aryl group, a heteroaryl group, a cycloalkyl group, or a heterocycloalkyl group which may have a substituent; and $R^{13}$ represents an aryl group, a heteroaryl group, a cycloalkyl group, a heterocycloalkyl group, a cycloalkenyl group, a heterocycloalkenyl group, an alkyl group, an alkenyl group, or an alkynyl group which may have a substituent.

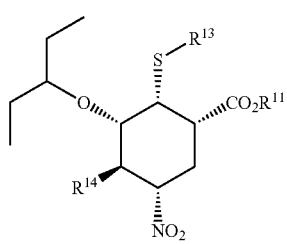

(B)

In the general formula (B), $R^{11}$ represents an alkyl group, an aryl group, a heteroaryl group, a cycloalkyl group, or a heterocycloalkyl group which may have a substituent; $R^{13}$ represents an aryl group, a heteroaryl group, a cycloalkyl group, a heterocycloalkyl group, a cycloalkenyl group, a heterocycloalkenyl group, an alkyl group, an alkenyl group, or an alkynyl group which may have a substituent; and $R^{14}$ represents a carboxyl group, a group in which a protecting group is bound to a carboxyl group, a halogenated carbonyl group, —C(=O)—$N_3$, —NCO, —$NAc_2$, or —NHAc.

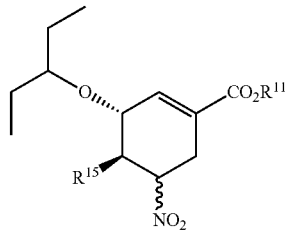

(C)

In the general formula (C), $R^{11}$ represents an alkyl group, an aryl group, a heteroaryl group, a cycloalkyl group, or a heterocycloalkyl group which may have a substituent; and $R^{15}$ represents a carboxyl group, or a group in which a protecting group is bound to a carboxyl group.

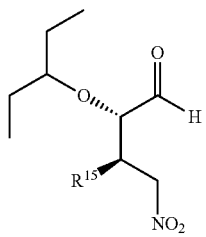

(C')

In the general formula (C'), $R^{15}$ represents a carboxyl group, or a group in which a protecting group is bound to a carboxyl group.

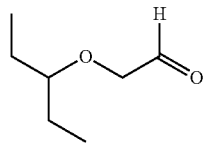

(D)

In the compound represented by the general formula (A), provided that $R^{10}$ is —$NAc_2$ or a carboxyl group, $R^{12}$ is a group in which a protecting group is bound to an amino group; and provided that $R^{10}$ is a group in which a protecting group is bound to a carboxyl group, $R^{12}$ is an amino group, a hydroxyamino group, or an alkoxyamino group. Moreover, although the protecting group of the amino group is not particularly limited, a tert-butoxycarbonyl group, a benzyloxycarbonyl group, a 9-fluorenylmethyloxycarbonyl group, a 2,2,2-trichloroethoxycarbonyl group, an allyloxycarbonyl group, a phthaloyl group, a p-toluenesulfonyl group, a p-nitrobenzenesulfonyl group, and the like may be exemplified. The protecting group of the carboxyl group may include a methyl ester group, an ethyl ester group, a benzyl ester group, a tert-butyl ester group, and the like. Moreover, in the general formula (A), the alkyl group represented by $R^{11}$ may be either linear or branched, and may have a substituent. Specifically, a methyl group, an ethyl group, a propyl group, and a tert-butyl group may be exemplified. In addition, the aryl group represented by Rn may have a substituent, and specifically, a naphthyl group, a tolyl group, a xylyl group, and the like may be exemplified. Of these, an ethyl group is preferred.

With respect to specific compounds, illustrative compounds represented by the general formula (A) include the following compounds (A-1) to (A-5).

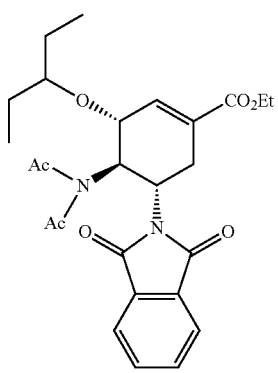

(A-1)

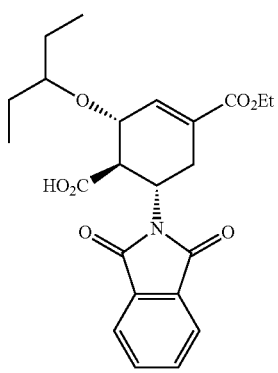

(A-2)

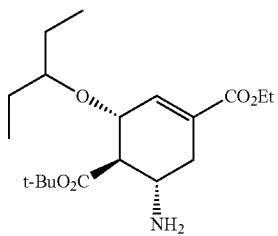

(A-3)

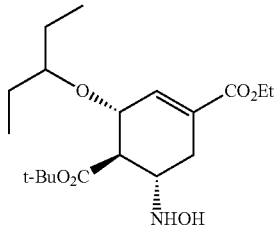

(A-4)

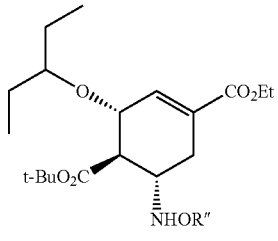

(A-5)

In the general formula (A-5), R″ represents a monovalent organic group.

In the general formula (A′), the alkyl group represented by $R^{11}$ may be either linear or branched, and may have a substituent. Specifically, a methyl group, an ethyl group, a propyl group, and a tert-butyl group may be exemplified. In addition, the aryl group represented by $R^{11}$ may have a substituent, and specifically, a naphthyl group, a tolyl group, a xylyl group, and the like may be exemplified. Of these, an ethyl group is preferred. Furthermore, $R^{13}$ is not particularly limited, and a p-methylphenyl group, a phenyl group, a naphthyl group, an ethyl group, a dodecyl group and the like may be exemplified, and a p-methylphenyl group is preferred.

With respect to specific compounds, illustrative compounds represented by the general formula (A′) include the following compound (A′-1).

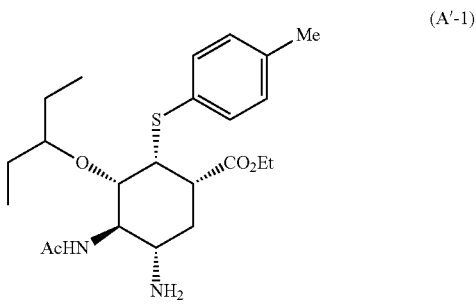

(A′-1)

In the compound represented by the general formula (B), the protecting group of the carboxyl group is as defined above. Moreover, in the general formula (B), the alkyl group represented by $R^{11}$ may be either linear or branched, and may have a substituent. Specifically, a methyl group, an ethyl group, a propyl group, and a tert-butyl group may be exemplified. In addition, the aryl group represented by $R^{11}$ may have a substituent, and specifically, a naphthyl group, a tolyl group, a xylyl group, and the like may be exemplified. Of these, an ethyl group is preferred. Furthermore, $R^{13}$ is not particularly limited, and a p-methylphenyl group, a phenyl group, a naphthyl group, an ethyl group, a dodecyl group and the like may be exemplified. A p-methylphenyl group is preferred.

With respect to specific compounds, illustrative compounds represented by the general formula (B) include the following compounds (B-1) to (B-7).

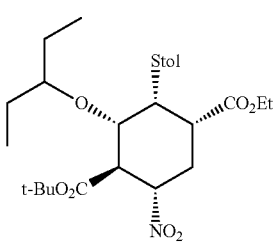

(B-1)

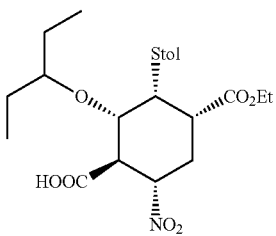

(B-2)

(B-3)
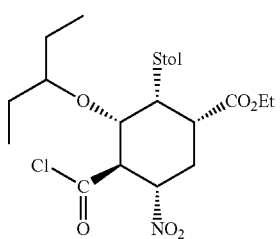

(B-4)
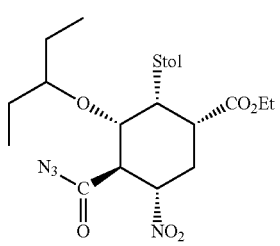

(B-5)
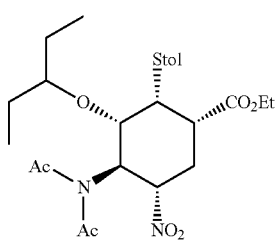

(B-6)
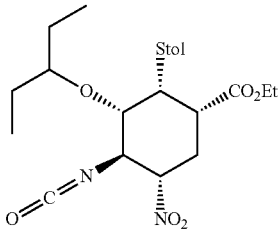

(B-7)
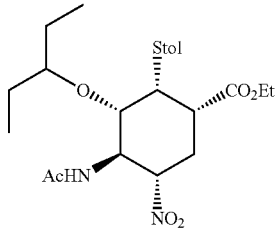

(C-1)
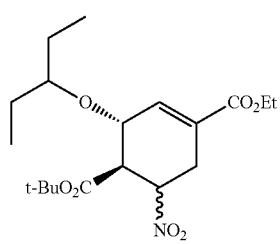

(C-2)
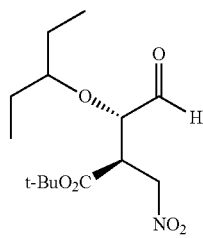

Furthermore, in the compound represented by the general formula (C'), the protecting group of the carboxyl group is as defined above.

With respect to specific compounds, illustrative compounds represented by the general formula (C') include the following compounds (C'-1) and (C'-2).

(C'-1)

(C'-2)
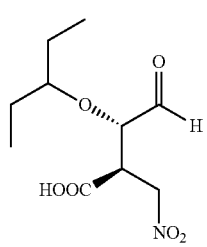

Also, in the compound represented by the general formula (C), the protecting group of the carboxyl group is as defined above. Moreover, in the general formula (C), the alkyl group represented by $R^{11}$ may be either linear or branched, and may have a substituent. Specifically, a methyl group, an ethyl group, a propyl group, and a tert-butyl group may be exemplified. In addition, the aryl group represented by $R^{11}$ may have a substituent, and specifically, naphthyl group, tolyl group, xylyl group, and the like may be exemplified. Of these, an ethyl group is preferred.

With respect to specific compounds, illustrative compounds represented by the general formula (C) include the following compounds (C-1) and (C-2).

EXAMPLES

Hereinafter, the present invention is explained in detail by way of Examples. It should be noted that the present invention is not any how limited to Examples shown below.

<Total Synthesis 1 of Oseltamivir Phosphate>

According to the following synthetic scheme, total synthesis of oseltamivir phosphate was carried out. The number of compounds set out in the following Reaction Examples is based on the number of the compounds in the synthetic scheme.

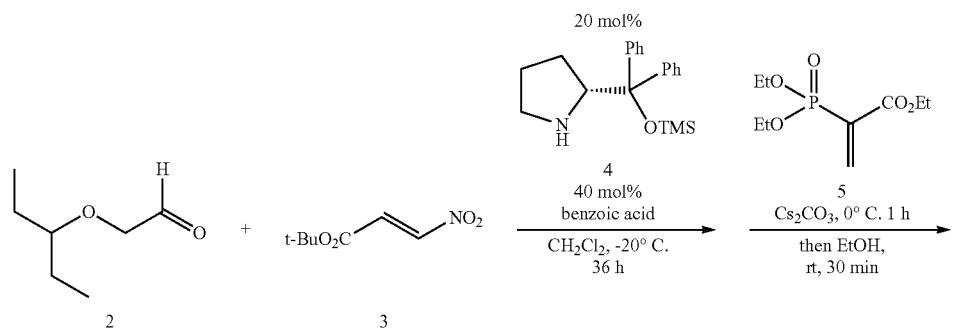
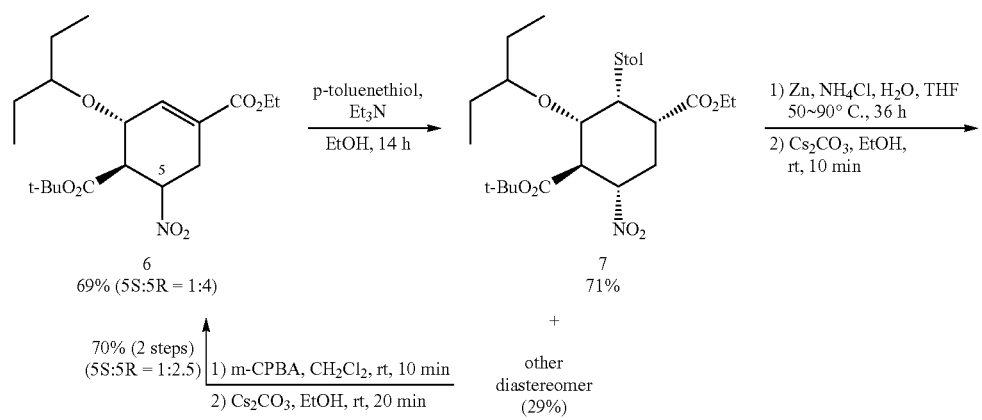
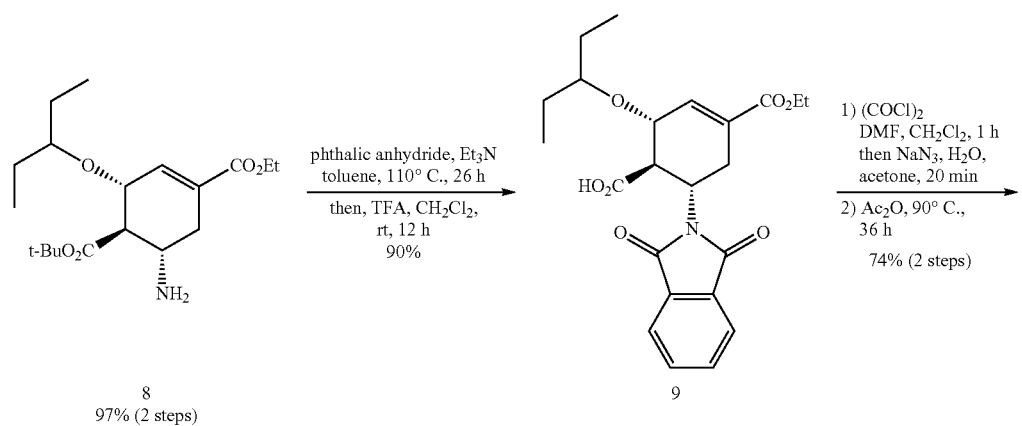
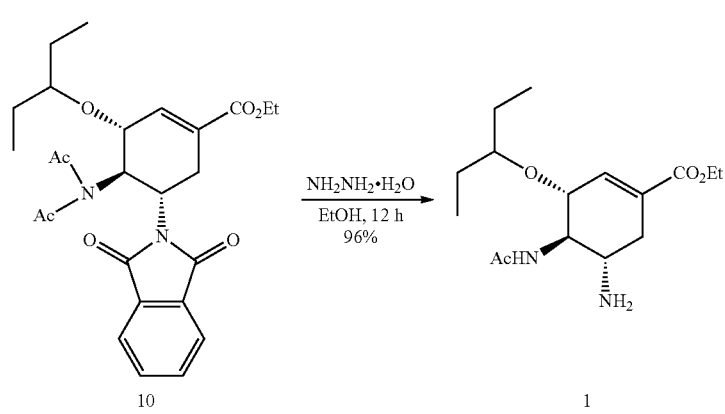

Reaction Example 1

Preparation of 3-(Allyloxy)pentane (Compound S1)

NaH (60% in oil, 2.76 g, 68.3 mmol) was added to a solution of 3-pentanol (4 g, 45.5 mmol) in tetrahydrofuran (20 mL) at 0° C. under argon atmosphere. The reaction mixture was stirred for 10 min at 0° C. followed by addition of allyl bromide (8.2 g, 68.3 mmol) and tetrabutylammonium iodide (60 mg, 0.016 mmol). The resulting mixture was stirred for 16 hrs at 23° C. before being quenched by addition of a saturated aqueous ammonium chloride solution. The organic layer was extracted with trichloromethane, washed with saturated aqueous sodium chloride, dried over magnesium sulfate, and concentrated under reduced pressure. Distillation at atmospheric pressure yielded 3-(allyloxy)pentane (compound S1, 4.8 g, yield 82%, boiling point 115° C. to 120° C.)

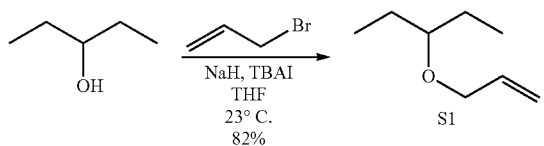

$^1$H NMR (400 MHz, CDCl$_3$) δ 5.93 (ddt, J=17.2, 10.4, 8.0 Hz, 1H), 5.26 (dd, J=17.2, 1.6 Hz, 1H), 5.13 (dd, J=10.4, 1.2 Hz, 1H), 3.98 (dd, J=8.0, 1.2 Hz, 2H), 3.17 (quintet, J=6.0 Hz, 1H), 1.51 (quintet, J=7.6 Hz, 4H), 0.90 (t, J=7.2 Hz, 6H).

Reaction Example 2

Preparation 1 of 2-(3-Pentyloxy)acetaldehyde (Compound 2)

Sodium periodate (13.4 g, 62.4 mmol) was added to a solution of the compound S1 (2 g, 15.6 mmol), osmium tetraoxide (0.02M t-butanol solution, 15.6 mL, 0.31 mmol) and 2,6-lutidine (3.64 mL, 31.2 mmol) in a mixed solvent of tetrahydrofuran (120 mL) and water (20 mL) at 23° C. under argon atmosphere. The reaction mixture was stirred for 2 hrs at 40° C. before being quenched with saturated aqueous sodium thiosulfate at 23° C. The organic layer was extracted with diethyl ether, washed with saturated aqueous copper sulfate and saturated aqueous sodium bicarbonate, dried over magnesium sulfate, and concentrated under reduced pressure. Flash chromatography (solid phase: SiO$_2$, mobile phase: 10% ethyl acetate-hexane) provided 2-(3-pentyloxy)acetaldehyde (compound 2, 890 mg, yield 44%).

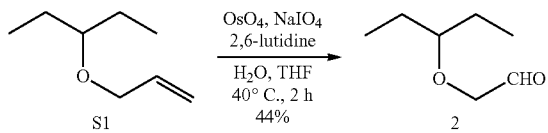

$^1$H NMR (400 MHz, CDCl$_3$) δ 9.76 (s, 1H), 4.05 (s, 2H), 3.30 (quintet, J=6.0 Hz, 1H), 1.55 (quintet, J=7.6 Hz, 4H), 0.93 (t, J=7.2 Hz, 6H);
$^{13}$C NMR (100 MHz, CDCl$_3$) δ 202.0, 83.4, 74.5, 25.6, 9.4;
IR (film) ν$_{max}$ 1736, 1462, 1382, 953 cm$^{-1}$;
HRMS (ESI) [M+Na]$^+$ calculated for [C$_7$H$_{14}$NaO$_2$]$^+$: 153.0886. found: 153.0887.

Reaction Example 3

Preparation of tert-Butyl 2-Hydroxy-3-nitropropanoate (Compound S2)

Sodium periodate (33.3 g, 156.4 mmol) was added to a solution of tert-butyl acrylate (5 g, 39.1 mmol), osmium tetraoxide (0.02M t-butanol solution, 39 mL, 0.78 mmol), and 2,6-lutidine (9.17 mL, 78.2 mmol) in a mixed solvent of tetrahydrofuran (300 mL) and water (100 mL) at 23° C. under argon atmosphere. The reaction mixture was stirred for 5 hrs at 40° C. before being quenched with saturated aqueous sodium thiosulfate at 23° C. The organic layer was extracted with trichloromethane, washed with saturated aqueous copper sulfate and saturated aqueous sodium bicarbonate, dried over magnesium sulfate, and concentrated under reduced pressure. The crude material was directly used in the next reaction.

Aluminum oxide (7.8 g, alumina) was added to a solution of the crude aldehyde in nitromethane (17 mL) at 23° C. under argon atmosphere. The resulting suspension was stirred for 18 hrs before removal of aluminum oxide by filtration. After the solvent was removed, flash chromatography (solid phase: SiO$_2$, mobile phase: 30% ethyl acetate-hexane) provided tert-butyl 2-hydroxy-3-nitropropanoate (compound S2, 5.36 g, yield 72% (2 steps)).

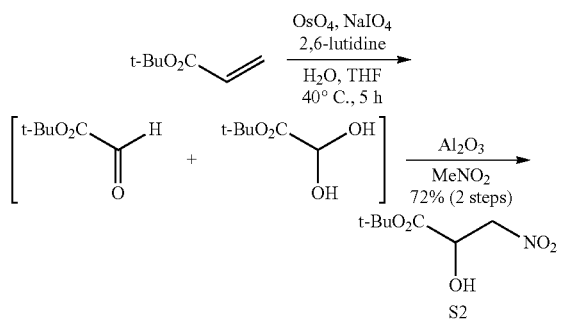

$^1$H NMR (400 MHz, CDCl$_3$) δ 4.71 (dd, J=4.4, 1.2 Hz, 2H), 4.49 (q, J=4.4 Hz, 1H), 3.13 (d, J=4.4 Hz, 1H), 1.53 (s, 9H);
$^{13}$C NMR (100 MHz, CDCl$_3$) δ 169.7, 84.6, 76.7, 67.6, 27.8;
IR (film) ν$_{max}$ 3371, 2986, 2924, 1730, 1560, 1460, 1421, 1214, 1157, 1124, 1033, 911, 871, 842 cm$^{-1}$;
HRMS (ESI) [M+Na]$^+$ calculated for [C$_7$H$_{13}$NNaO$_5$]$^+$: 214.0682. found: 214.0686.

Reaction Example 4

Preparation of (E)-tert-Butyl 3-Nitroacrylate (Compound 3)

Methanesulfonyl chloride (1.6 mL, 21.3 mmol) was added to a solution of the compound S2 (1.36 g, 7.1 mmol), triethylamine (1.5 mL, 21.3 mmol) and dichloromethane (8 mL) at −20° C. under argon atmosphere. The reaction mixture was stirred for 1 hour at −20° C. before being quenched by addition of water. The organic layer was extracted with diethyl ether, washed with saturated aqueous copper sulfate and saturated aqueous sodium bicarbonate, dried over magnesium sulfate, and concentrated under reduced pressure. Flash chromatography (solid phase: SiO$_2$, mobile phase: 5% ethyl acetate-hexane) provided (E)-tert-butyl 3-nitroacrylte (compound 3, 933 mg, yield 76%).

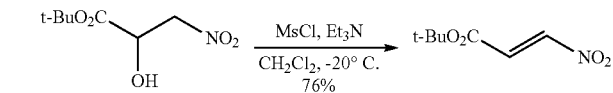

$^1$H NMR (400 MHz, CDCl$_3$) δ 7.58 (d, J=17.6 Hz, 1H), 7.00 (d, J=17.6 Hz, 1H), 1.52 (s, 9H).

Reaction Example 5

Preparation 1 of (3R,4R,5S or R)-4-tert-Butyl-1-ethyl-5-nitro-3-(3-pentyloxy)cyclohex-1-ene-1,4-dicarboxylate (Compound 6)

Benzoic acid (56.8 mg, 0.46 mmol) was added to a solution of the compound 2 (222.6 mg, 1.71 mmol), the compound 3 (200 mg, 1.16 mmol) and (R)-diphenylprolinol trimethylsilyl ether (compound 4, 84.8 mg, 0.23 mmol) in dichloromethane (2 mL) at −20° C. under argon atmosphere. The reaction mixture was stirred for 36 hrs at −20° C. followed by addition of ethyl-2-(diethoxyphosphoryl)-acrylate (compound 5, 399.8 mg, 16.9 mmol) and cesium carbonate (1.88 g, 5.78 mmol) at the same temperature. After the resulting suspension was stirred for an additional 1 hour at 0° C., ethanol (4 mL) was added to the reaction mixture. The resulting reaction mixture was stirred for an additional 30 min at 23° C. before being quenched with saturated aqueous ammonium chloride.

The organic layer was extracted with trichloromethane, washed with saturated aqueous sodium chloride, dried over magnesium sulfate, and concentrated under reduced pressure. Flash chromatography provided (3R,4R,5S or R)-4-tert-butyl-1-ethyl-5-nitro-3-(3-pentyloxy)cyclohex-1-ene-1,4-dicarboxylate (compound 6, 305.2 mg, yield 69% calculated from the compound 3 as a standard, C-5 diastereomer mixture (5S:5R=1:4)) and (3S,4R,5R)-4-tert-butyl-1-ethyl-5-nitro-3-(3-pentyloxy)cyclohex-1-ene-1,4-dicarboxylate (compound S3, 31.2 mg, 7%). The diastereomer mixture of the compound 6 was employed in the next reaction.

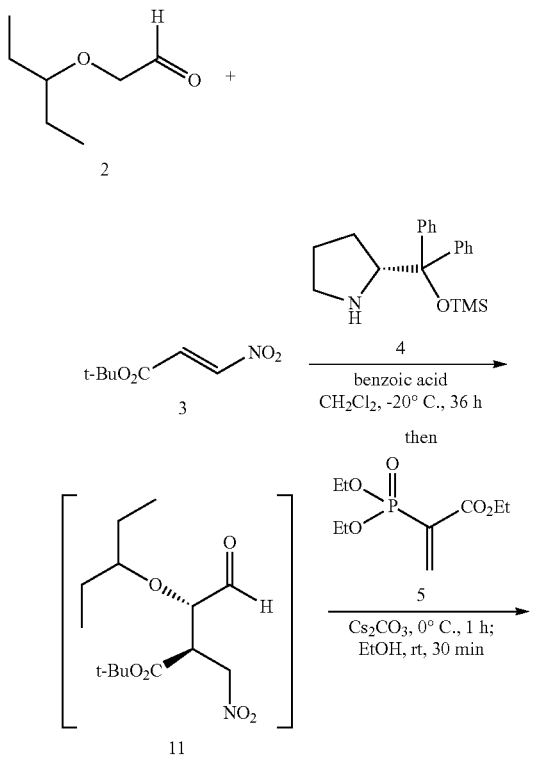

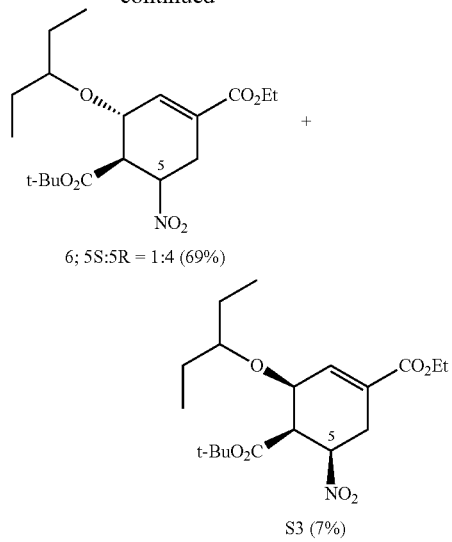

All spectral data were collected after mild acidic isomerization on silica gel (Wakogel B-5F purchased from Wako Pure Chemical Industries, Tokyo, Japan) for 40 minutes. Final diastereomer ratio was 5S:5R=1.29:1.

For major diastereomer of the compound 6 (5S): $^1$H NMR (400 MHz, CDCl$_3$) δ 6.85 (br s, 1H), 4.75-4.90 (m, 1H), 4.39 (d, J=8.4 Hz, 1H), 4.20 (q, J=6.8 Hz, 2H), 3.71 (br s, 1H), 3.32 (quintet, J=6.0 Hz, 1H), 3.00-3.12 (m, 1H), 2.80 (br dd, J=16.8, 10.8 Hz, 1H), 1.45-1.65 (m, 4H), 1.47 (s, 9H), 1.28 (t, J=7.2 Hz, 3H), 0.78-0.98 (m, 6H).

For major diastereomer of the compound 6 (5R): $^1$H NMR (400 MHz, CDCl$_3$) δ 6.89 (br s, 1H), 4.75-4.90 (m, 1H), 4.51 (br s, 1H), 4.12-4.25 (m, 1H), 4.20 (q, J=6.8 Hz, 2H), 3.44 (quintet, J=6.0 Hz, 1H), 2.92-3.20 (m, 2H), 1.45-1.65 (m, 4H), 1.39 (s, 9H), 1.28 (t, J=7.2 Hz, 3H), 0.78-0.98 (m, 6H).

As diastereomer mixture of the compound 6: $^{13}$C NMR (100 MHz, CDCl$_3$) δ 170.0, 167.5, 165.5, 165.1, 137.6, 135.0, 129.5, 127.2, 83.0, 82.6, 82.2, 81.8, 81.4, 78.0, 73.1, 70.8, 61.2, 61.1, 50.3, 47.6, 28.7, 27.8 (4C), 27.7 (2C), 26.4, 26.3, 25.8, 25.7, 25.4, 14.1 (2C), 9.9, 9.5, 9.3, 9.2;

IR (film) ν$_{max}$ 2975, 2937, 2878, 1721, 1660, 1557, 1461, 1369, 1302, 1253, 1158, 1098, 1059, 1021 cm$^{-1}$;

HRMS (ESI) [M+Na]$^+$ calculated for [C$_{19}$H$_{31}$NNaO$_7$]$^+$: 408.1993. found: 408.1983.

For the compound S3 (3S,4R,5R): $^1$H NMR (400 MHz, CDCl$_3$) δ 6.84 (br s, 1H), 4.72 (ddd, J=10.4, 6.0, 4.0 Hz, 1H), 4.35-4.40 (m, 1H), 4.20 (q, J=7.2 Hz, 2H), 3.63 (dd, J=6.4, 4.0 Hz, 1H), 3.44 (quintet, J=5.6 Hz, 1H), 3.27 (ddt, J=17.6, 10.4, 2.8 Hz, 1H), 2.98 (dd, J=17.6, 6.4 Hz, 1H), 1.48-1.60 (m, 4H), 1.42 (s, 9H), 1.30 (t, J=7.2 Hz, 3H), 0.87 (t, J=7.2 Hz, 3H), 0.86 (t, J=7.2 Hz, 3H);

$^{13}$C NMR (100 MHz, CDCl$_3$) δ 166.7, 165.4, 137.7, 127.9, 81.9, 80.2, 72.6, 61.0, 46.3, 27.8 (3C), 26.5, 25.7 (2C), 25.3, 14.2, 9.2, 9.1;

IR (film) ν$_{max}$ 2968, 2937, 2879, 1729, 1654, 1554, 1462, 1369, 1258, 1241, 1151, 1096, 1062, 736 cm$^{-1}$;

HRMS (ESI) [M+Na]$^+$ calculated for [C$_{19}$H$_{31}$NNaO$_7$]$^+$: 408.1993. found: 408.2006;

[α]$^{23}$$_D$ +22.7 (c 1.40, CHCl$_3$).

Reaction Example 6

Preparation of (2R,3S)-tert-Butyl-2-(nitromethyl)-4-oxo-3-(3-pentyloxy)butanoate (Compound 11) for the Determination of Enantiomeric Excess Benzoic acid (14.1 mg, 0.12 mmol) was added to a solution of the compound 2 (56.4 mg, 0.43 mmol), the compound 3 (50 mg, 0.29 mmol), and (R)-diphenylprolinol trimethylsilyl ether (compound 4, 18.8 mg, 0.58 mmol) in dichloromethane (2 mL) at −20° C. under argon atmosphere. The reaction mixture was stirred for 36 hrs at −20° C. before being quenched with saturated aqueous sodium bicarbonate. The organic layer was extracted with trichloromethane, washed with saturated aqueous sodium chloride, dried over magnesium sulfate, and concentrated under reduced pressure. Flash chromatography (solid phase: $SiO_2$, mobile phase: 5% ethyl acetate-hexane to 20% ethyl acetate-hexane) provided (2R, 3S)-tert-butyl-2-(nitromethyl)-4-oxo-3-(3-pentyloxy)butanoate (compound 11, 87.8 mg, quantitative yield, C-2 diastereomer mixture (syn: anti=5:1, enantiomeric excess of syn-isomer: 95% ee, enantiomeric excess of anti-isomer: 96% ee)).

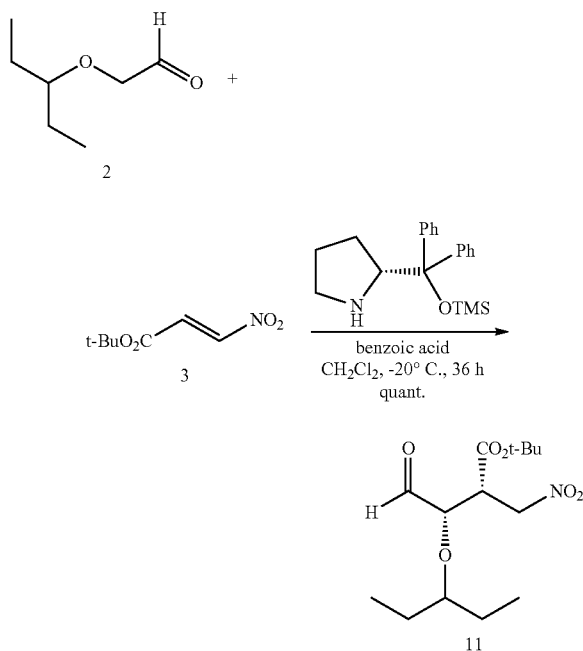

For HPLC analysis, the compound 11 was converted to (4R,5R,E)-6-tert-butyl-1-ethyl-5-(nitromethyl)-4-(3-pentyloxy)hexa-2-enedioate (compound S4) by addition of 1.5 equivalent of ethyl(triphenylphosphoranylidene)acetate in benzene (23° C., 14 hrs, yield 97% as diastereomer mixture), and enantiomeric excess was determined by HPLC with a Chiralpak IC Column (trade name, manufactured by Dicel Chemical. Industries Ltd., mobile phase 1:200=2-propanol: hexane), 1 mL/min. syn-major enantiomer $t_R$=62.2 min, syn-minor enantiomer $t_R$=41.9 min, anti-major enantiomer $t_R$=85.0 min, anti-minor enantiomer $t_R$=46.9 min.

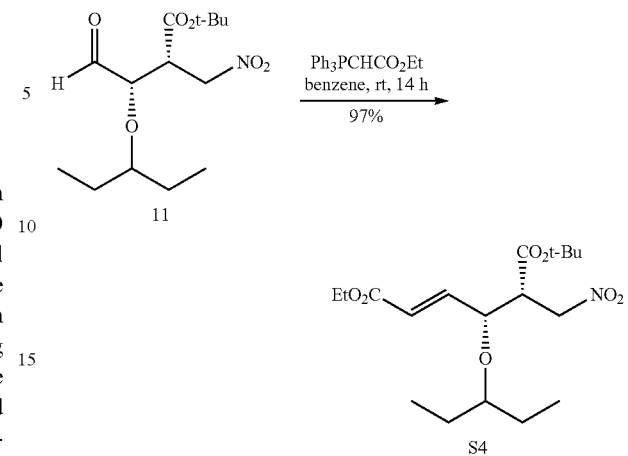

For major syn diastereomer (compound 11): $^1$H NMR (400 MHz, $CDCl_3$) δ 9.72 (s, 1H), 4.83 (dd, J=14.4, 8.0 Hz, 1H), 4.45 (dd, J=14.0, 6.0 Hz, 1H), 3.98 (d, J=3.2 Hz, 1H), 3.73 (ddd, J=8.0, 6.0, 3.0 Hz, 1H), 3.19 (quintet, J=6.0 Hz, 1H), 1.45-1.62 (m, 4H), 1.42 (s, 9H), 0.94 (t, J=7.2 Hz, 3H), 0.88 (t, J=7.2 Hz, 3H);

$^{13}$C NMR (100 MHz, $CDCl_3$) δ 201.7, 167.0, 83.5, 83.3, 79.5, 72.2, 46.5, 27.8 (3C), 26.0, 25.1, 9.2 (2C);

IR (film) $v_{max}$ 2972, 2937, 2879, 1735, 1560, 1460, 1424, 1370, 1253, 1210, 1157, 1105, 843 cm$^{-1}$;

HRMS (ESI) [M+Na]$^+$ calculated for $[C_{14}H_{25}NNaO_6]^+$: 326.1574. found: 326.1575.

Reaction Example 7

Preparation 1 of (1S,2R,3S,4R,5S)-4-tert-Butyl-1-ethyl-5-nitro-3-(3-pentyloxy)-2-(p-tolylthio)cyclohexane-1,4-dicarboxylate (Compound 7)

Toluenethiol (29 mg, 0.234 mmol) was added to a solution of the compound 6 (18 mg, 0.0468 mmol, C-5 diastereomer mixture (5S:5R=1:4)) and triethylamine (19.6 mL, 0.14 mmol) in ethanol (1 mL) at 23° C. under argon atmosphere. The reaction mixture was stirred for 12 hrs at 23° C. under reduced pressure. Flash chromatography (solid phase: $SiO_2$, mobile phase: 5% ethyl acetate-hexane to 10% ethyl acetate-hexane) provided (1S,2R,3S,4R,5S)-4-tert-butyl-1-ethyl-5-nitro-3-(3-pentyloxy)-2-(p-tolylthio)cyclohexane-1,4-dicarboxylate (compound 7, 17.0 mg, yield 71%) and other enantiomer mixture S5 (6.8 mg, yield 21%).

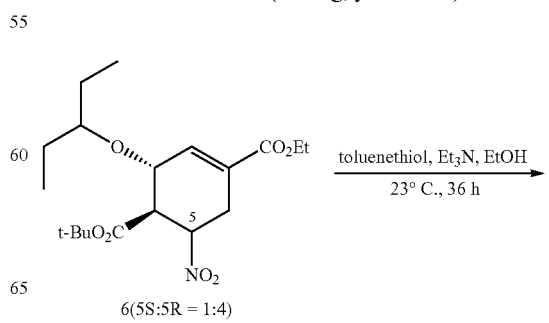

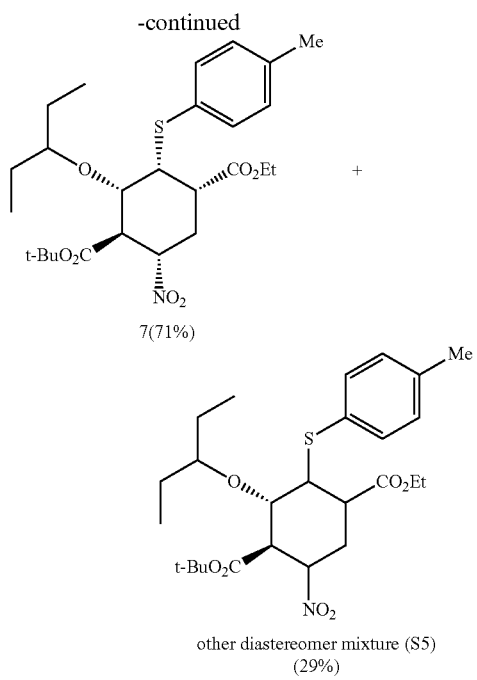

7(71%)

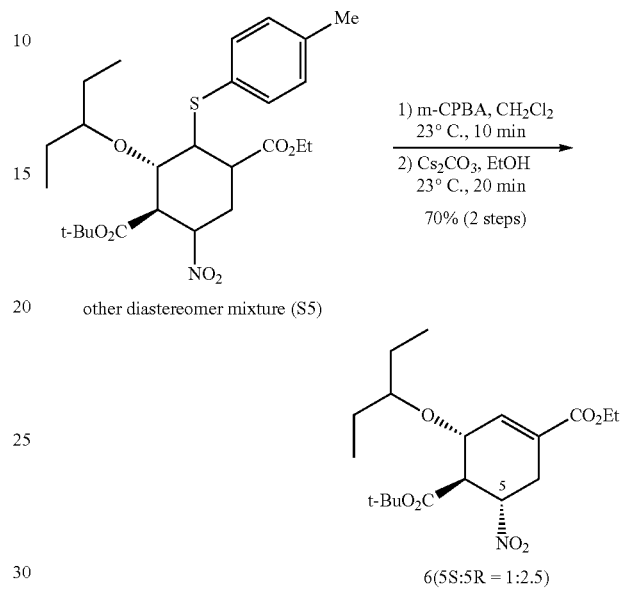

other diastereomer mixture (S5)
(29%)

For the compound 7: $^1$H NMR (400 MHz, CDCl$_3$) δ 7.38 (d, J=8.4 Hz, 2H), 7.07 (d, J=8.4 Hz, 2H), 4.59 (dt, J=4.4, 12.4 Hz, 1H), 4.00-4.12 (m, 2H), 3.75-3.90 (m, 2H), 3.27 (t, J=11.2 Hz, 1H), 3.21 (quintet, J=5.6 Hz, 1H), 2.73 (dt, J=13.2, 3.2 Hz, 1H), 2.55 (dt, J=13.2, 3.6 Hz, 1H), 2.39 (q, J=13.2 Hz, 1H), 2.30 (s, 3H), 1.45 (s, 9H), 1.20-1.50 (m, 4H), 1.16 (t, J=7.2 Hz, 3H), 0.76 (t, J=7.2 Hz, 3H), 0.67 (t, J=7.2 Hz, 3H);

$^{13}$C NMR (100 MHz, CDCl$_3$) δ 170.7, 170.0, 137.4, 132.7 (2C), 131.2, 129.5 (2C), 83.8, 82.3, 79.0, 75.7, 61.4, 521, 49.7, 43.3, 27.9 (3C), 26.9, 24.9, 23.4, 21.0, 14.0, 8.7, 8.6;

IR (film) ν$_{max}$ 2977, 2933, 2878, 1731, 1553, 1492, 1460, 1368, 1292, 1253, 1198, 1157, 1136, 1097, 1030, 955, 811 cm$^{-1}$;

HRMS (ESI) [M+Na]$_1$ calculated for [C$_{26}$H$_{39}$NNaO$_7$S]$_1$: 532.2339. found: 532.2319; [α]$_D^{20}$ –18.2 (c 1.09, CHCl$_3$).

Reaction Example 8

Preparation 2 of (3R,4R,5S, or R)-4-tert-Butyl-1-ethyl-5-nitro-3-(3-pentyloxy)cyclohex-1-ene-1,4-dicarboxylate (Compound 6)

m-Chloroperbenzoic acid (5.3 mg, 0.0246 mmol, purity 77%) was added to a solution of compound S5 (8 mg, 0.0157 mmol, diastereomer mixture) in dichloromethane (0.5 mL) at 23° C. under argon atmosphere. The reaction mixture was stirred for 10 min at 23° C. before being quenched by addition of pH 7.0 phosphate buffer solution. The organic layer was extracted with ethyl acetate, washed with saturated aqueous sodium chloride, dried over magnesium sulfate, and concentrated under reduced pressure. Crude material in an amount of 13 mg was obtained.

Cesium carbonate (50 mg, 0.154 mmol) was added to a solution of 13 mg of the crude material in ethanol (1 mL) at 23° C. under argon atmosphere. The reaction mixture was stirred for 20 min at 23° C. before being quenched with excess amount of water. The organic layer was extracted with trichloromethane, washed with saturated aqueous sodium chloride, dried over magnesium sulfate, and concentrated under reduced pressure. Preparative thin layer chromatography (solid phase: SiO$_2$, mobile phase: 10% ethyl acetate-hexane) provided (3R,4R,5S, or R)-4-tert-butyl-1-ethyl-5-nitro-3-(3-pentyloxy)cyclohex-1-ene-1,4-dicarboxylate (compound 6, 4.2 mg, yield 70% (2 steps), C-5 diastereomer mixture (5S:5R=1:2.5)).

Reaction Example 9

Preparation of (3R,4R,5S)-tert-Butyl-1-ethyl-5-amino-3-(3-pentyloxy)cyclohex-1-ene-1,4-dicarboxylate (Compound 8)

Activated zinc powder (1 g, washed with 1 N hydrochloric acid, water, ethanol, and diethyl ether before using) was added to a solution of the compound 7 (19 mg, 0.0373 mmol) in tetrahydrofuran (0.5 mL) and saturated aqueous ammonium chloride (0.5 mL) at 23° C. under argon atmosphere. The reaction mixture was stirred for 1 hour at 50° C. followed by additional stirring for 36 hrs at 90° C. before filtrating off the zinc powder. 28% Aqueous ammonium hydroxide solution was added to the filtrate. The organic layer was extracted with 10% methanol/trichloromethane, washed with saturated aqueous sodium chloride, dried over magnesium sulfate, and concentrated under reduced pressure to provide a crude material (18 mg).

Cesium carbonate (50 mg, 0.154 mmol) was added to a solution of 18 mg of the crude material in ethanol (1 mL) at 23° C. under argon atmosphere. The reaction mixture was stirred for 10 min at 23° C. before being quenched by addition of an excess amount of water. The organic layer was extracted with 10% methanol/trichloromethane, washed with saturated aqueous sodium chloride, dried over magnesium sulfate, and concentrated under reduced pressure. Pencil column (solid phase: SiO$_2$, mobile phase: 10% ethyl acetate-hexane to 100% ethyl acetate) provided (3R,4R,5S)-tert-butyl-1-ethyl-5-amino-3-(3-pentyloxy)cyclohex-1-ene-1,4-dicarboxylate (compound 8, 12.8 mg, yield 97% (2 steps)).

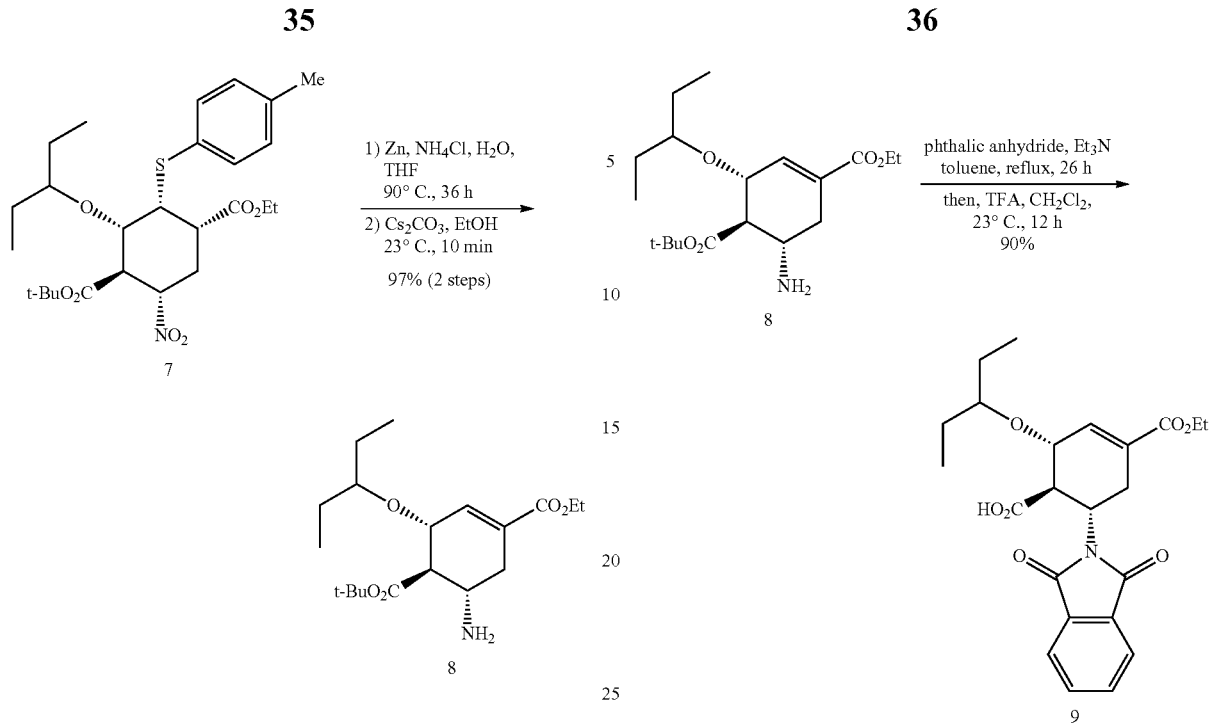

$^1$H NMR (400 MHz, CDCl$_3$) δ 6.83 (br s, 1H), 4.32-4.38 (m, 1H), 4.17 (q, J=7.2 Hz, 2H), 3.03 (quintet, J=5.6 Hz, 1H), 3.15 (dt, J=5.6, 10.8 Hz, 1H), 2.67 (dd, J=17.6, 5.6 Hz, 1H), 2.33 (dd, J=10.8, 9.2 Hz, 1H), 2.01 (ddt, J=17.6, 5.6, 3.2 Hz, 1H), 1.40-1.55 (m, 4H), 1.50 (s, 9H), 1.26 (t, J=7.2 Hz, 3H), 0.89 (t, J=7.2 Hz, 3H), 0.83 (t, J=7.2 Hz, 3H), —NH$_2$ undetected;

$^{13}$C NMR (100 MHz, CDCl$^3$) δ 173.1, 166.4, 138.0, 129.3, 81.4, 81.0, 74.4, 60.8, 56.5, 49.3, 34.0, 28.2 (3C), 25.9, 25.6, 14.2, 9.5, 9.4;

IR (film) μ$_{max}$ 3445, 2979, 2935, 2877, 1716, 1652, 1458, 1392, 1367, 1247, 1202, 1154, 1059 cm$^{-1}$;

HRMS (ESI) [M+Na]$^+$ calculated for [C$_{29}$H$_{33}$NNaO$_5$]$^+$: 378.2251. found: 328.2259;

[α]$^{20}{}_D$ –28.4 (c 0.55, CHCl$_3$).

Reaction Example 10

Preparation of (1R,2R,6S)-6-(1,3-Dioxoisoindolin-2-yl)-4-(ethoxycarbonyl)-2-(3-pentyloxy)cyclohex-3-enecarboxylic Acid (Compound 9)

Phthalic anhydride (9.2 mg, 0.062 mmol) was added to a solution of the compound 8 (11 mg, 0.031 mmol) and triethylamine (43.2 μL, 0.31 mmol) in toluene (0.5 mL) at 23° C. under argon atmosphere. The reaction mixture was stirred for 26 hrs at 110° C. before removing the solvent and excess triethylamine under reduced pressure. Trifluoroacetic acid (0.5 mL) was added to the reaction mixture at 23° C. under argon atmosphere after adding 0.5 mL of dichloromethane as a solvent. The resulting reaction mixture was stirred for an additional 12 hrs at 23° C. before the solvent was removed under reduced pressure. Preparative thin layer chromatography (solid phase: SiO$_2$, mobile phase: 50% ethyl acetate-hexane) afforded (1R,2R,6S)-6-(1,3-dioxoisoindolin-2-yl)-4-(ethoxycarbonyl)-2-(3-pentyloxy)cyclohex-3-enecarboxylic acid (compound 9, 11.9 mg, 90%).

$^1$H NMR (400 MHz, CDCl$_3$) δ 7.83 (dd, J=5.6, 3.2 Hz, 2H), 7.71 (dd, J=5.6, 3.2 Hz, 2H), 6.88 (br s, 1H), 4.60 (dt, J=5.6, 11.2 Hz, 1H), 4.45-4.54 (m, 1H), 4.19 (q, J=7.2 Hz, 2H), 3.59 (dd, J=12.4, 9.6 Hz, 1H), 3.33 (quintet, J=5.6 Hz, 1H), 3.04 (ddt, J=14.4, 11.2, 3.2 Hz, 1H), 2.58 (dd, J=14.4, 5.6 Hz, 1H), 1.51 (quintet, J=7.6 Hz, 2H), 1.35 (quintet, J=7.6 Hz, 2H), 1.26 (t, J=7.2 Hz, 3H), 0.90 (t, J=7.2 Hz, 3H), 0.68 (t, J=7.2 Hz, 3H), —CO$_2$H undetected; $^{13}$C NMR (100 MHz, CDCl$_3$) δ 176.2, 167.5 (2C), 165.7, 137.7 (2C), 134.2 (2C), 131.6, 129.0, 123.5 (2C), 81.7, 74.5, 61.0, 48.5, 47.1, 28.0, 26.3, 25.2, 14.2, 9.6, 9.0;

IR (film) ν$_{max}$ 3214, 2967, 2935, 2877, 1776, 1718, 1468, 1374, 1335, 1262, 1192, 1110, 1056, 1013, 978, 942, 876, 795, 720 cm$^{-1}$;

HRMS (ESI) [M+Na]$^+$ calculated for [C$_{23}$H$_{27}$NNaO$_7$]$^+$: 452.1680. found: 452.1666;

[α]$^{23}{}_D$ –33.7 (c 1.33, CHCl$_3$).

Reaction Example 11

Preparation of (3R,4R,5S)-ethyl-4-(N-Acetylacetamide)-5-(1,3-dioxoisoindolin-2-yl)-3-(3-pentyloxy)cyclohex-1-ene Carboxylate (Compound 10)

Oxalyl chloride (27.8 μL, 0.33 mmol) was added to a solution of the compound 9 (14 mg, 0.033 mmol) and a catalytic amount of dimethylformamide (one drop) in dichloromethane (2 mL) at 0° C. under argon atmosphere. The reaction mixture was stirred for 1 hour at 23° C. before the solvent was removed under reduced pressure. Saturated aqueous sodium azide (0.3 mL) was added thereto at 0° C. after adding 1 mL of acetone as a solvent. The reaction mixture was stirred for 20 min at the same temperature before being quenched by addition of excess water (10 mL). The organic layer was extracted with trichloromethane, washed with saturated aqueous sodium chloride, dried over magnesium sulfate, and concentrated under reduced pressure to provide a crude material.

The crude material was dissolved in acetic anhydride (2 mL), and the solution was stirred for 36 hrs at 90° C. before the solvent was removed under reduced pressure. Preparative chromatography (solid phase: SiO$_2$, mobile phase: ethyl acetate-hexane) afforded (3R,4R,5S)-ethyl-4-(N-acetyl acetamide)-5-(1,3-dioxoisoindolin-2-yl)-3-(3-pentyloxy)cyclohex-1-ene carboxylate (compound 10, 11.7 mg, yield 74%, 94% ee (2 steps)).

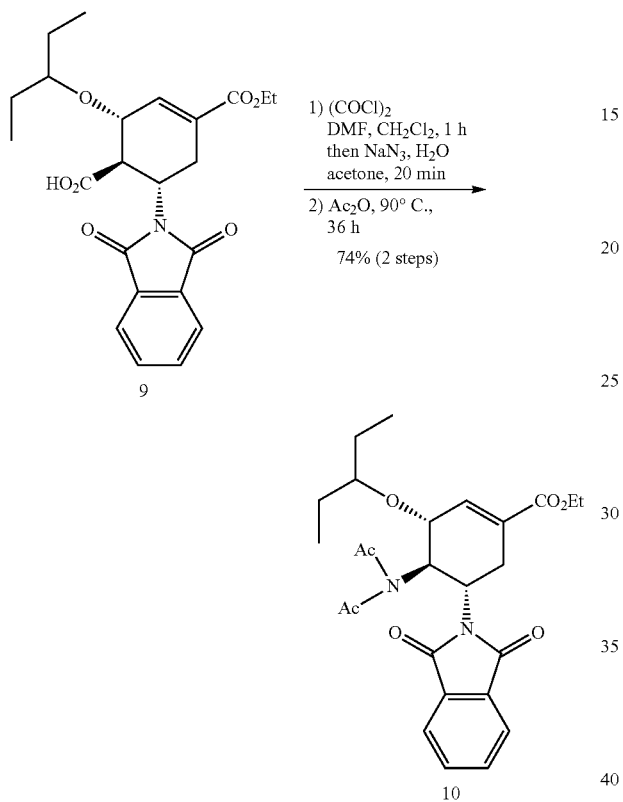

$^1$H NMR (400 MHz, CDCl$_3$) δ 7.81 (dd, J=5.6, 3.2 Hz, 2H), 7.71 (dd, J=5.6, 3.2 Hz, 2H), 6.89 (t, J=2.0 Hz, 1H), 5.35 (dt, J=5.6, 11.2 Hz, 1H), 4.96 (br d, J=7.6 Hz, 1H), 4.71 (dd, J=11.6, 9.7 Hz, 1H), 4.20 (q, J=7.2 Hz, 2H), 3.33 (quintet, J=5.6 Hz, 1H), 2.98 (ddt, J=14.4, 11.2, 3.2 Hz, 1H), 2.70 (dd, J=17.2, 5.2 Hz, 1H), 2.47 (s, 3H), 2.18 (s, 3H), 1.32-1.60 (m, 4H), 1.28 (t, J=7.2 Hz, 3H), 0.92 (t, J=7.2 Hz, 3H), 0.77 (t, J=7.2 Hz, 3H);

$^{13}$C NMR (100 MHz, CDCl$_3$) δ 175.9, 175.0, 165.8, 138.1 (2C), 134.3 (2C), 131.4, 128.9, 123.5 (2C), 81.0, 73.1, 61.0, 60.3, 45.9, 29.7, 27.6, 25.9, 24.8, 24.6, 14.2, 9.5, 8.8 (carbonyl group on phtalimide undetected);

IR (film) v$_{max}$ 2967, 2934, 1777, 1716, 1467, 1376, 1253, 1221, 1189, 1107, 1056, 986, 722 cm$^{-1}$;

HRMS (ESI) [M+Na]$^+$ calculated for [C$_{26}$H$_{32}$N$_2$NaO$_7$]$^+$: 507.2102. found: 507.2088;

[α]$^{23}{}_D$ −47.9 (c 1.47, CHCl$_3$).

Enantiomeric excess of the compound 10 was determined by HPCL with a Chiralpak IC Column (trade name, manufactured by Dicel Chemical. Industries Ltd., mobile phase 1:20=2-propanol:hexane) at 1 mL/min; major enantiomer t$_R$=41.2 min, minor enantiomer t$_R$=29.7 min.

Reaction Example 12

Preparation of (−)-Oseltamivir (Compound 1)

Hydrazine monohydrate (15 μL, 0.31 mmol) was added to a solution of the compound 10 (30 mg, 0.062 mmol) in ethanol (0.5 mL) at 23° C. under argon atmosphere. The reaction mixture was stirred for 14 hrs at 50° C. before being quenched with 1 N hydrochloric acid (3 mL). The water phase was washed with ethyl acetate followed by an adjustment to pH 11 with 28% ammonium hydroxide in water. The organic phase was extracted with 10% methanol/trichloromethane, washed with saturated aqueous sodium chloride, dried over magnesium sulfate, and concentrated under reduced pressure to afford (−)-oseltamivir (compound 1, 18.5 mg, 96%).

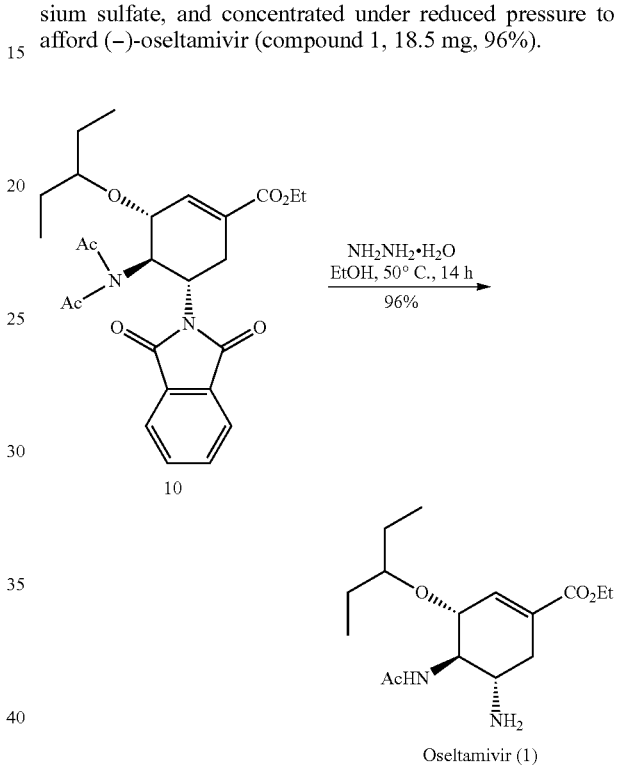

$^1$H NMR (400 MHz, CDCl$_3$) δ 6.78 (t, J=2.0 Hz, 1H), 5.62 (d, J=7.6 Hz, 1H), 4.20 (q, J=7.2 Hz, 2H), 4.15-4.20 (m, 1H), 3.52 (q, J=8.0 Hz, 1H), 3.34 (quintet, J=5.6 Hz, 1H), 3.24 (dt, J=5.2, 10.0 Hz, 1H), 2.75 (dd, J=17.6, 5.2 Hz, 1H), 2.15 (ddt, J=17.6, 10.0, 2.8 Hz, 1H), 2.04 (s, 3H), 1.40-1.60 (m, 4H), 1.29 (t, J=7.2 Hz, 3H), 0.90 (t, J=7.2 Hz, 3H), 0.89 (t, J=7.2 Hz, 3H), —NH$_2$ undetected;

$^{13}$C NMR (100 MHz, CDCl$_3$) δ 170.9, 166.3, 137.5, 129.6, 81.7, 74.8, 60.8, 59.0, 49.2, 33.6, 26.3, 25.8, 23.7, 14.2, 9.5, 9.3;

IR (film) v$_{max}$ 3276, 3077, 2965, 2936, 2877, 1715, 1655, 1558, 1464, 1374, 1303, 1244, 1195, 1127, 1064, 1031, 944, 861, 778, 736 cm$^{-1}$;

HRMS (ESI) [M+Na]$^+$ calculated for [C$_{26}$H$_{28}$N$_2$NaO$_4$]$^+$: 335.1941. found: 335.1934;

[α]$^{23}{}_D$ −54.9 (c 0.68, CHCl$_3$).

<Total Synthesis 2 of Oseltamivir Phosphate>

Total synthesis of oseltamivir phosphate was carried out according to the following synthetic scheme. The number of compounds set out in the following Reaction Examples is based on the number of the compounds in the synthetic scheme. It is to be noted that description of reactions identical to those in Total Synthesis 1 of Oseltamivir Phosphate may be omitted.

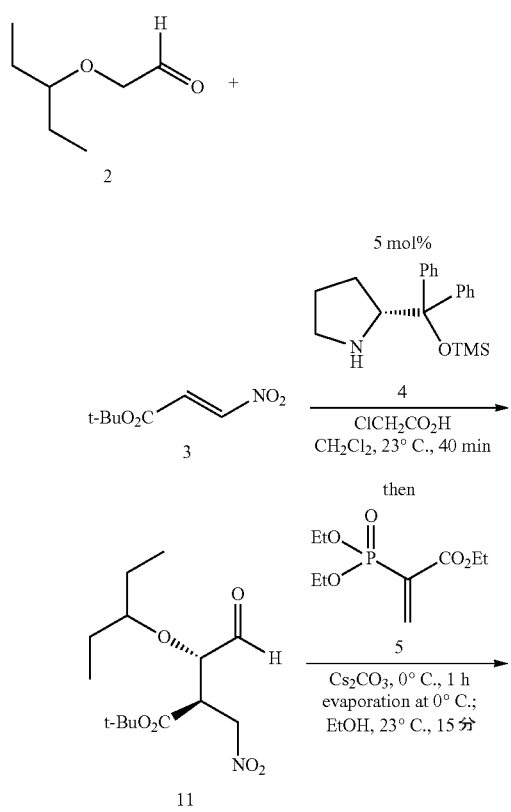
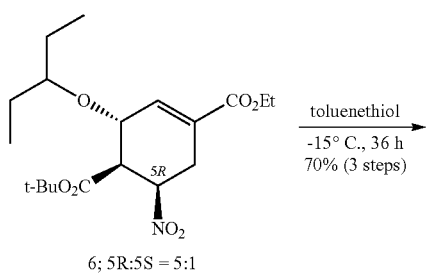
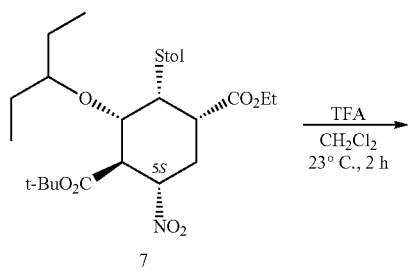
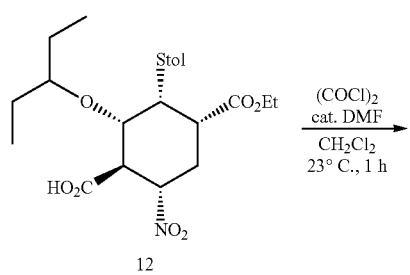
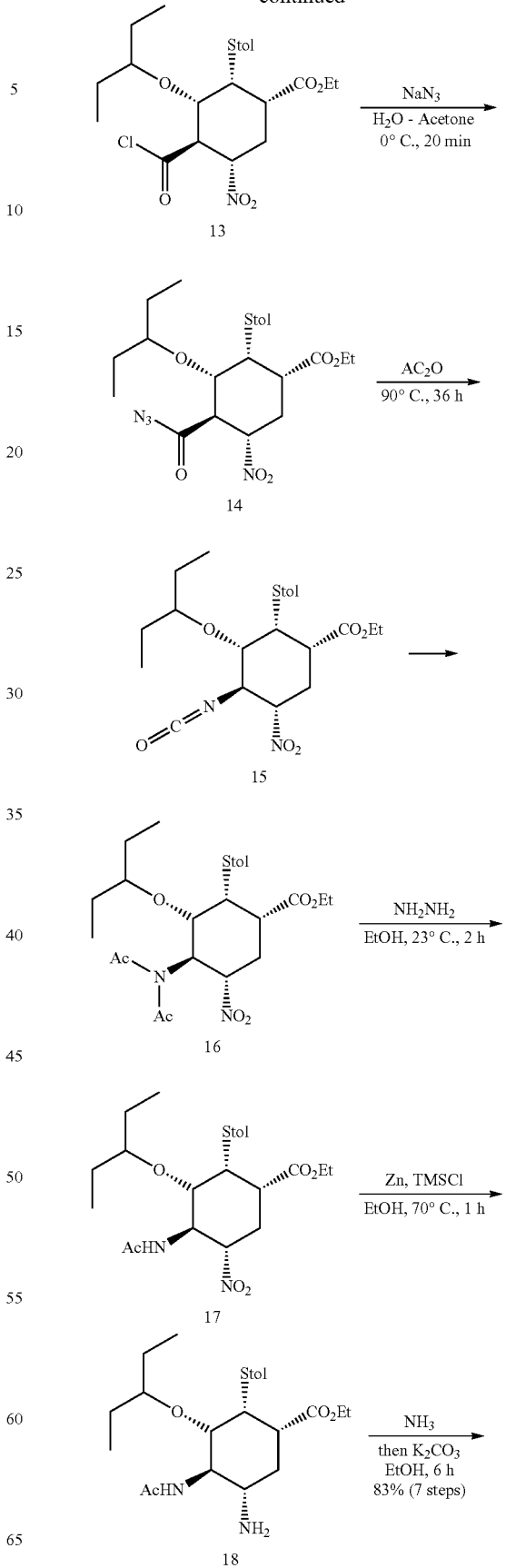

-continued

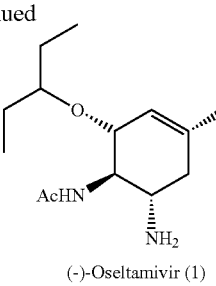

(−)-Oseltamivir (1)

Reaction Example 13

Preparation 2 of 2-(3-Pentanyloxy)acetaldehyde (Compound 2)

Sodium periodate (18.4 g, 86.0 mmol) was added to a solution of the compound S1 (2.76 g, 21.5 mmol) and osmium tetraoxide (0.02 M t-butanol solution, 21.5 mL, 0.43 mmol) in tetrahydrofuran (170 mL) and water (175 mL) at 23° C. under argon atmosphere. The reaction mixture was stirred for 5 hrs at 70° C. before being quenched by addition of saturated aqueous sodium thiosulfate at 23° C. The aqueous layer was extracted three times with diethyl ether. The combined organic layer was washed with saturated aqueous sodium chloride, dried over magnesium sulfate, and concentrated under reduced pressure. The crude material was subjected to distillation (22 Torr, boiling point 61° C.) to afford 2-(3-pentyloxy)acetaldehyde (compound 2, 1.73 g, yield 62%).

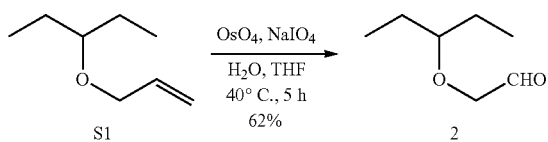

$^1$H NMR (400 MHz, CDCl$_3$) δ 9.76 (s, 1H), 4.05 (s, 2H), 3.30 (quintet, J=6.0 Hz, 1H), 1.55 (quintet, J=7.6 Hz, 4H), 0.93 (t, J=7.2 Hz, 6H);
$^{13}$C NMR (100 MHz, CDCl$_3$) δ 202.0, 83.4, 74.5, 25.6, 9.4;
IR (film) $v_{max}$ 1736, 1462, 1382, 953 cm$^{-1}$;
HRMS (ESI) [M+Na]$^+$ calculated for [C$_7$H$_{14}$NaO$_2$]$^+$: 153.0886. found: 153.0887.

Reaction Example 14

Preparation of (2R,3S)-tert-Butyl-2-(nitromethyl)-4-oxo-3-(3-pentanyloxy)butanoate (Compound 11)

Chloroacetic acid (3.5 mg, 0.037 mmol) was added to a solution of the compound 2 (35.8 mg, 0.278 mmol), the compound (32 mg, 0.185 mmol) and (R)-diphenylprolinol trimethylsilyl ether (compound 4, 3.0 mg, 0.0093 mmol) in dichloromethane (0.5 mL) at 23° C. under argon atmosphere. The reaction mixture was stirred for 1 hour at 23° C. before being quenched with saturated aqueous sodium bicarbonate. The aqueous layer was extracted three times with trichloromethane. The combined organic layer was washed with saturated aqueous sodium chloride, dried over magnesium sulfate, and concentrated under reduced pressure. Flash chromatography (solid phase: SiO$_2$, mobile phase: concentration gradient in n-hexane of from 5% ethyl acetate to 20% ethyl acetate) provided (2R,3S)-tert-butyl-2-(nitromethyl)-4-oxo-3-(3-pentanyloxy)butanoate (compound 11, C-2 diastereomer mixture, syn: anti=5:1, syn-isomer: 96% ee, anti-isomer: 87% ee).

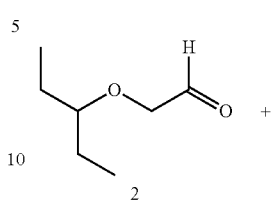

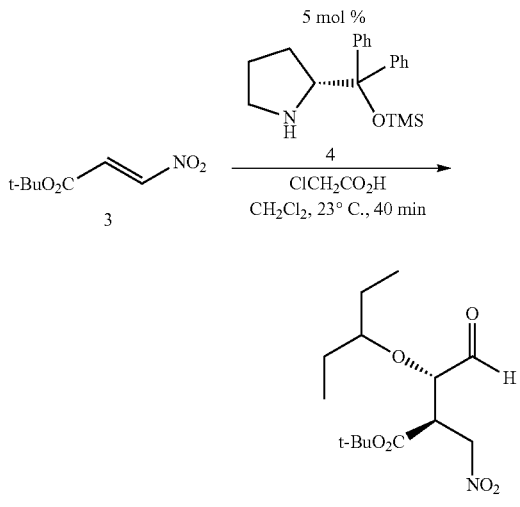

For major syn diastereomer (compound 11): $^1$H NMR (400 MHz, CDCl$_3$) δ 9.72 (s, 1H), 4.83 (dd, J=14.4, 8.0 Hz, 1H), 4.45 (dd, J=14.0, 6.0 Hz, 1H), 3.98 (d, J=3.2 Hz, 1H), 3.73 (ddd, J=8.0, 6.0, 3.0 Hz, 1H), 3.19 (quintet, J=6.0 Hz, 1H), 1.45-1.62 (m, 4H), 1.42 (s, 9H), 0.94 (t, J=7.2 Hz, 3H), 0.88 (t, J=7.2 Hz, 3H);
$^{13}$C NMR (100 MHz, CDCl$_3$) δ 201.7, 167.0, 83.5, 83.3, 79.5, 72.2, 46.5, 27.8 (3C), 26.0, 25.1, 9.2 (2C);
IR (film) $v_{max}$ 2972, 2937, 2879, 1735, 1560, 1460, 1424, 1370, 1253, 1210, 1157, 1105, 843 cm$^{-1}$;
HRMS (ESI) [M+Na]$^+$ calculated for [C$_{14}$H$_{25}$NNaO$_6$]$^+$: 326.1574. found: 326.1575.

For HPLC analysis, the compound 11 was converted to (4R,5R,E)-6-tert-butyl-1-ethyl-5-(nitromethyl)-4-(3-pentyloxy)hexa-2-enedioate (compound S4) by addition of 1.5 equivalent of ethyl(triphenylphosphoranylidene)acetate in benzene (23° C., 14 hrs, yield 94% as diastereomer mixture), and enantiomeric excess was determined by HPLC with a Chiralpak IC Column (trade name, manufactured by Dicel Chemical. Industries Ltd., mobile phase 1:200=2-propanol: n-hexane), 1 mL/min.

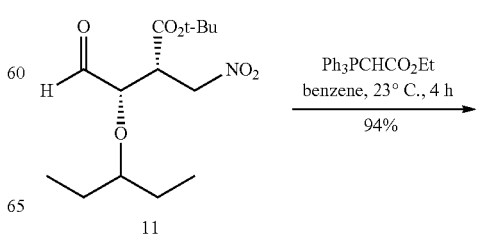

-continued

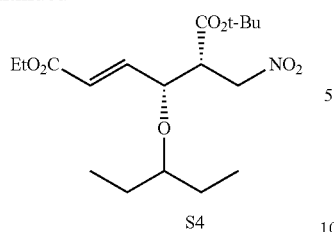

S4

1 mL/min; syn-major enantiomer $t_R$=56.4 min, syn-minor enantiomer $t_R$=38.5 min, anti-major enantiomer $t_R$=76.5 min, anti-minor enantiomer $t_R$=42.5 min.

Reaction Example 15

Preparation 2 of (3R,4R,5S or R)-4-tert-Butyl-1-ethyl-5-nitro-3-(3-pentyloxy)cyclohex-1-ene-1,4-Dicarboxylate (Compound 6)

Chloroacetic acid (2.7 mg, 0.029 mmol) was added to a solution of the compound 2 (28.0 mg, 0.217 mmol), the compound (25 mg, 0.145 mmol), and (R)-diphenylprolinol trimethylsilyl ether (compound 4, 2.34 mg, 0.007 mmol) in dichloromethane (1.5 mL) at 23° C. under argon atmosphere. The reaction mixture was stirred for 1.5 hrs at 23° C. followed by addition of ethyl-2-(diethoxyphosphoryl)-acrylate (compound 5, 51.2 mg, 0.217 mmol) and cesium carbonate (235.0 mg, 0.723 mmol) at 0° C. After the resulting mixture was stirred for an additional 3 hrs at 0° C., ethanol (1 mL) was added thereto. The resulting mixture was stirred for an additional 20 min at 23° C. before being quenched by addition of saturated aqueous ammonium chloride. The aqueous layer was extracted with trichloromethane three times. The combined organic layer was washed with saturated aqueous sodium chloride, dried over magnesium sulfate, and concentrated under reduced pressure. As crude material being unstable a quick flash column chromatography (solid phase: SiO$_2$, mobile phase: 10% ethyl acetate-n-hexane solution) provided (3R,4R,5S or R)-4-tert-butyl-1-ethyl-5-nitro-3-(3-pentyloxy)cyclohex-1-ene-1,4-dicarboxylate (compound 6, 40.5 mg, yield 73% calculated from the compound 3, C-5 diastereomer mixture (5S:5R=1:4)) and (3S,4R,5R)-4-tert-butyl-1-ethyl-5-nitro-3-(3-pentyloxy)cyclohex-1-ene-1,4-dicarboxylate (compound S3, 5.6 mg, yield 10%). The diastereomer mixture of the compound 6 was employed in the next reaction.

All spectral data of the compound 6 were collected after mild acidic isomerization on the silica gel (Wakogel B-5F purchased from Wako Pure Chemical Industries, Tokyo, Japan) for 40 minutes. Final diastereomer ratio was 5S:5R=1.29:1.

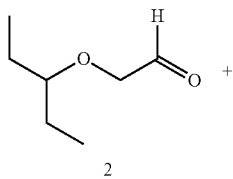

2

-continued

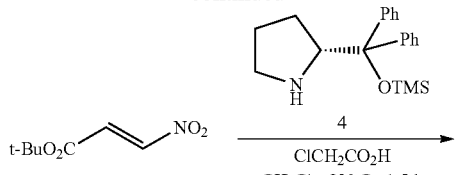

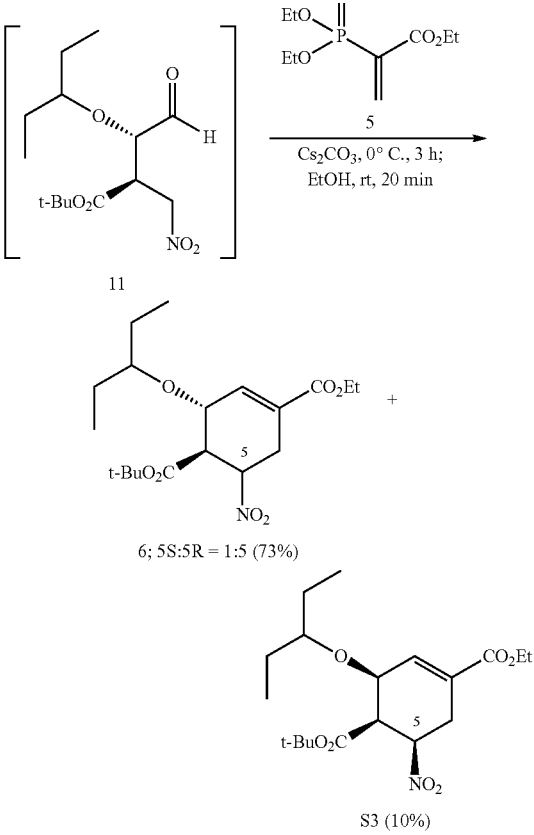

For major diastereomer of the compound 6 (5S): $^1$H NMR (400 MHz, CDCl$_3$) δ 6.85 (br s, 1H), 4.75-4.90 (m, 1H), 4.39 (d, J=8.4 Hz, 1H), 4.20 (q, J=6.8 Hz, 2H), 3.71 (br s, 1H), 3.32 (quintet, J=6.0 Hz, 1H), 3.00-3.12 (m, 1H), 2.80 (br dd, J=16.8, 10.8 Hz, 1H), 1.45-1.65 (m, 4H), 1.47 (s, 9H), 1.28 (t, J=7.2 Hz, 3H), 0.78-0.98 (m, 6H).

For major diastereomer of the compound 6 (5R): $^1$H NMR (400 MHz, CDCl$_3$) δ 6.89 (br s, 1H), 4.75-4.90 (m, 1H), 4.51 (br s, 1H), 4.12-4.25 (m, 1H), 4.20 (q, J=6.8 Hz, 2H), 3.44 (quintet, J=6.0 Hz, 1H), 2.92-3.20 (m, 2H), 1.45-1.65 (m, 4H), 1.39 (s, 9H), 1.28 (t, J=7.2 Hz, 3H), 0.78-0.98 (m, 6H).

As diastereomer mixture of the compound 6: $^{13}$C NMR (100 MHz, CDCl$_3$) δ 170.0, 167.5, 165.5, 165.1, 137.6, 135.0, 129.5, 127.2, 83.0, 82.6, 82.2, 81.8, 81.4, 78.0, 73.1, 70.8, 61.2, 61.1, 50.3, 47.6, 28.7, 27.8 (4C), 27.7 (2C), 26.4, 26.3, 25.8, 25.7, 25.4, 14.1 (2C), 9.9, 9.5, 9.3, 9.2;

IR (film) $v_m$, 2975, 2937, 2878, 1721, 1660, 1557, 1461, 1369, 1302, 1253, 1158, 1098, 1059, 1021 cm$^{-1}$;

HRMS (ESI) [M+Na]$^+$ calculated for [C$_{19}$H$_{31}$NNaO$_7$]$^+$: 408.1993, found: 408.1983.

For the compound S3 (3S,4R,5R): $^1$H NMR (400 MHz, CDCl$_3$) δ 6.84 (br s, 1H), 4.72 (ddd, J=10.4, 6.0, 4.0 Hz, 1H), 4.35-4.40 (m, 1H), 4.20 (q, J=7.2 Hz, 2H), 3.63 (dd, J=6.4, 4.0

Hz, 1H), 3.44 (quintet, J=5.6 Hz, 1H), 3.27 (ddt, J=17.6, 10.4, 2.8 Hz, 1H), 2.98 (dd, J=17.6, 6.4 Hz, 1H), 1.48-1.60 (m, 4H), 1.42 (s, 9H), 1.30 (t, J=7.2 Hz, 3H), 0.87 (t, J=7.2 Hz, 3H), 0.86 (t, J=7.2 Hz, 3H);

$^{13}$C NMR (100 MHz, CDCl$_3$) δ 166.7, 165.4, 137.7, 127.9, 81.9, 80.2, 72.6, 61.0, 46.3, 27.8 (3C), 26.5, 25.7 (2C), 25.3, 14.2, 9.2, 9.1;

IR (film) $v_{max}$ 2968, 2937, 2879, 1729, 1654, 1554, 1462, 1369, 1258, 1241, 1151, 1096, 1062, 736 cm$^{-1}$;

HRMS (ESI) [M+Na]$^+$ calculated for [C$_{19}$H$_{31}$NNaO$_7$] 408.1993. found: 408.2006;

$[\alpha]^{23}_D$+22.7 (c 1.40, CHCl$_3$).

Reaction Example 16

Preparation 2 of (1S,2R,3S,4R,5S)-4-tert-Butyl-1-ethyl-5-nitro-3-(3-pentyloxy)-2-(p-tolylthio)cyclohexane-1,4-dicarboxylate (Compound 7)

Toluenethiol (46.5 mg, 0.374 mmol) was added to a solution of the compound 6 (14.4 mg, 0.0374 mmol, C-5 diastereomer mixture; 5S:5R=1:4.6) and cesium carbonate (61 mg, 0.187 mmol) in ethanol (1 mL) at −40° C. under argon atmosphere. The reaction mixture was slowly warmed to −15° C. and stirred for 45 hrs before being quenched by addition of 1 N hydrochloric acid. The aqueous layer was extracted three times with trichloroacetic acid. The combined organic layer was washed with saturated aqueous sodium chloride, dried over magnesium sulfate, and concentrated under reduced pressure. Flash chromatography (solid phase: SiO$_2$, mobile phase: concentration gradient in hexane of from 5% ethyl acetate to 10% ethyl acetate) provided (1S,2R,3S,4R,5S)-4-tert-butyl-1-ethyl-5-nitro-3-(3-pentyloxy)-2-(p-tolylthio)cyclohexane-1,4-dicarboxylate (compound 7, 17.2 mg, yield 90%).

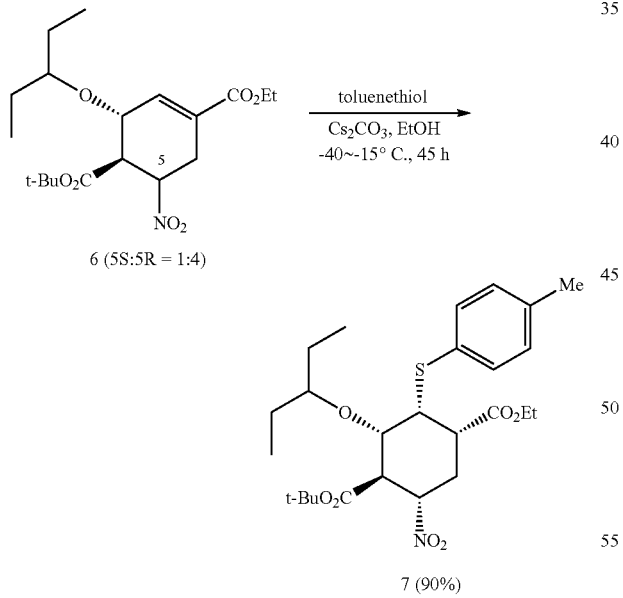

6 (5S:5R = 1:4)

7 (90%)

$^1$H NMR (400 MHz, CDCl$_3$) δ 7.38 (d, J=8.4 Hz, 2H), 7.07 (d, J=8.4 Hz, 2H), 4.59 (dt, J=4.4, 12.4 Hz, 1H), 4.00-4.12 (m, 2H), 3.75-3.90 (m, 2H), 3.27 (t, J=11.2 Hz, 1H), 3.21 (quintet, J=5.6 Hz, 1H), 2.73 (dt, J=13.2, 3.2 Hz, 1H), 2.55 (dt, J=13.2, 3.6 Hz, 1H), 2.39 (q, J=13.2 Hz, 1H), 2.30 (s, 3H), 1.45 (s, 9H), 1.20-1.50 (m, 4H), 1.16 (t, J=7.2 Hz, 3H), 0.76 (t, J=7.2 Hz, 3H), 0.67 (t, J=7.2 Hz, 3H);

$^{13}$C NMR (100 MHz, CDCl$_3$) δ 170.7, 170.0, 137.4, 132.7 (2C), 131.2, 129.5 (2C), 83.8, 82.3, 79.0, 75.7, 61.4, 52.1, 49.7, 43.3, 27.9 (3C), 26.9, 24.9, 23.4, 21.0, 14.0, 8.7, 8.6;

IR (film) $v_m$ 2977, 2933, 2878, 1731, 1553, 1492, 1460, 1368, 1292, 1253, 1198, 1157, 1136, 1097, 1030, 955, 811 cm$^{-1}$;

HRMS (ESI) [M+Na]$^+$ calculated for [C$_{26}$H$_{39}$NNaO$_7$S]$^+$: 532.2339. found: 532.2319;

$[\alpha]^{20}_D$−18 (c 1.09, CHCl$_3$).

Reaction Example 17

One-Pot Reaction from Compounds 2 and 3 to Compound 7

Chloroacetic acid (21.8 mg, 0.231 mmol) was added to a solution of the compound 2 (225 mg, 1.73 mmol), the compound 3 (200 mg, 1.16 mmol) and (R)-diphenylprolinol triethylsilyl ether (compound 4, 18.8 mg, 0.058 mmol) in dichloromethane (2 mL) at 23° C. under argon atmosphere. The reaction mixture was stirred for 40 min at 23° C. followed by addition of ethyl-2-(diethoxyphosphoryl)-acrylate (compound 5, 409.2 mg, 1.73 mmol) and cesium carbonate (1.13 g, 3.47 mmol) at 0° C. After the resulting reaction mixture was stirred for an additional 3 hrs at 0° C., the solvent was removed under reduced pressure at 0° C., and ethanol (3 mL) was added thereto. The reaction mixture was stirred for 15 min at 23° C. before addition of toluenethiol (716.7 mg, 5.78 mmol) at −15° C. The resulting mixture was stirred for 36 hrs at −15° C. before being quenched by addition of cold 2 N hydrochloric acid. The aqueous layer was extracted three times with trichloromethane. The combined organic layer was washed with saturated aqueous sodium bicarbonate, dried over magnesium sulfate, and concentrated under reduced pressure. Flash chromatography (solid phase: SiO$_2$, mobile phase: concentration gradient in n-hexane of from 5% ethyl acetate to 10% ethyl acetate) provided (1S,2R,3S,4R,5S)-4-tert-butyl-1-ethyl-5-nitro-3-(3-pentyloxy)-2-(p-tolylthio)cyclohexane-1,4-dicarboxylate (compound 7, 413.7 mg, yield 70% calculated from the compound 3 as a standard).

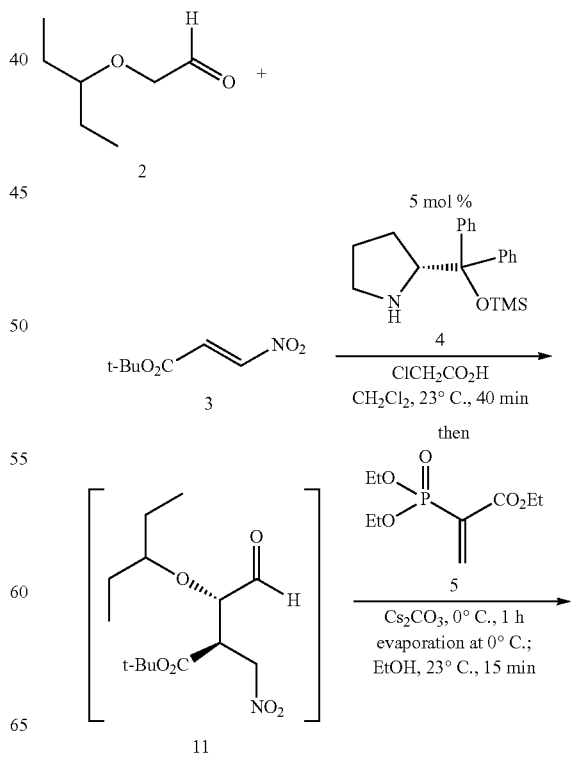

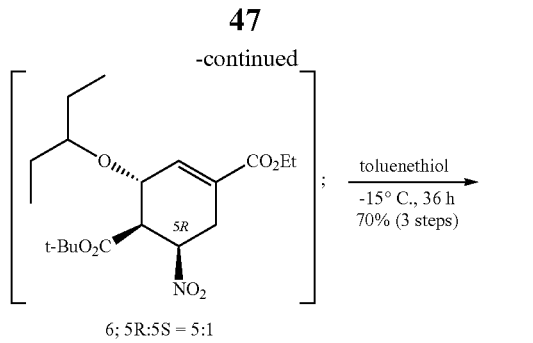

6; 5R:5S = 5:1

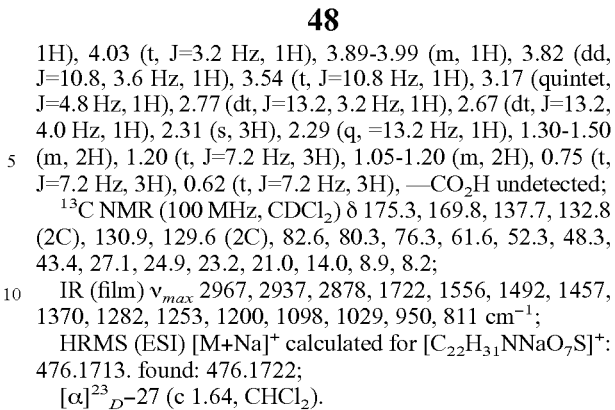

Reaction Example 18

Preparation of (1R,2S,3R,4S,6S)-4-(Ethoxycarbonyl)-6-nitro-2-(3-pentanyloxy)-3-(p-tolylthio)cyclohexane-Carboxylic Acid (Compound 12)

Trifluoroacetic acid (1.5 mL) was added to a solution of the compound 7 (180 mg, 0.354 mmol) in dichloromethane (1.5 mL) at 23° C. under argon atmosphere. The reaction mixture was stirred for 2 hrs at 23° C. before removing the solvent and trifluoroacetic acid. Flash column chromatography (solid phase: SiO$_2$, mobile phase: 70% ethyl acetate-n-hexane solution) provided (1R,2S,3R,4S,6S)-4-(ethoxycarbonyl)-6-nitro-2-(3-pentanyloxy)-3-(p-tolylthio)cyclohexane-carboxylic acid (compound 12, 141.7 mg, yield 88%).

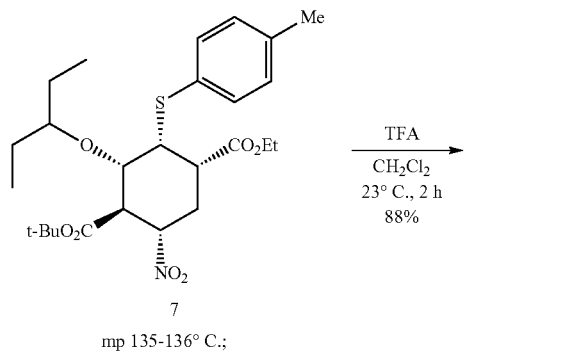

7
mp 135-136° C.;

12

$^1$H NMR (400 MHz, CDCl$_2$) δ 7.39 (d, J=8.0 Hz, 2H), 7.07 (d, J=8.0 Hz, 2H), 4.66 (dt, J=4.8, 12.0 Hz, 1H), 4.09-4.20 (m, 1H), 4.03 (t, J=3.2 Hz, 1H), 3.89-3.99 (m, 1H), 3.82 (dd, J=10.8, 3.6 Hz, 1H), 3.54 (t, J=10.8 Hz, 1H), 3.17 (quintet, J=4.8 Hz, 1H), 2.77 (dt, J=13.2, 3.2 Hz, 1H), 2.67 (dt, J=13.2, 4.0 Hz, 1H), 2.31 (s, 3H), 2.29 (q, =13.2 Hz, 1H), 1.30-1.50 (m, 2H), 1.20 (t, J=7.2 Hz, 3H), 1.05-1.20 (m, 2H), 0.75 (t, J=7.2 Hz, 3H), 0.62 (t, J=7.2 Hz, 3H), —CO$_2$H undetected;

$^{13}$C NMR (100 MHz, CDCl$_2$) δ 175.3, 169.8, 137.7, 132.8 (2C), 130.9, 129.6 (2C), 82.6, 80.3, 76.3, 61.6, 52.3, 48.3, 43.4, 27.1, 24.9, 23.2, 21.0, 14.0, 8.9, 8.2;

IR (film) ν$_{max}$ 2967, 2937, 2878, 1722, 1556, 1492, 1457, 1370, 1282, 1253, 1200, 1098, 1029, 950, 811 cm$^{-1}$;

HRMS (ESI) [M+Na]$^+$ calculated for [C$_{22}$H$_{31}$NNaO$_7$S]$^+$: 476.1713. found: 476.1722;

[α]$^{23}_D$ –27 (c 1.64, CHCl$_2$).

Reaction Example 19

Preparation of (1S,2R,3S,4R,5S)-Ethyl 4-(chlorocarbonyl)-5-nitro-3-(3-pentanyloxy)-(p-tolylthio)cyclohexane Carboxylate (Compound 13)

To a solution of the compound 12 (11 mg, 0.0216 mmol) in dichloromethane (1 mL) were added a catalytic amount of dimethyl formamide (1 μL) and oxalyl chloride (20 μL, 0.216 mmol) at 0° C. The resulting mixture was stirred for 1 hour at 23° C., and the solvent and excess oxalyl chloride were removed under reduced pressure to provide (1S,2R,3S,4R,5S)-ethyl 4-(chlorocarbonyl)-5-nitro-3-(3-pentanyloxy)-(p-tolylthio)cyclohexane carboxylate (compound 13, 10 mg, yield 98%).

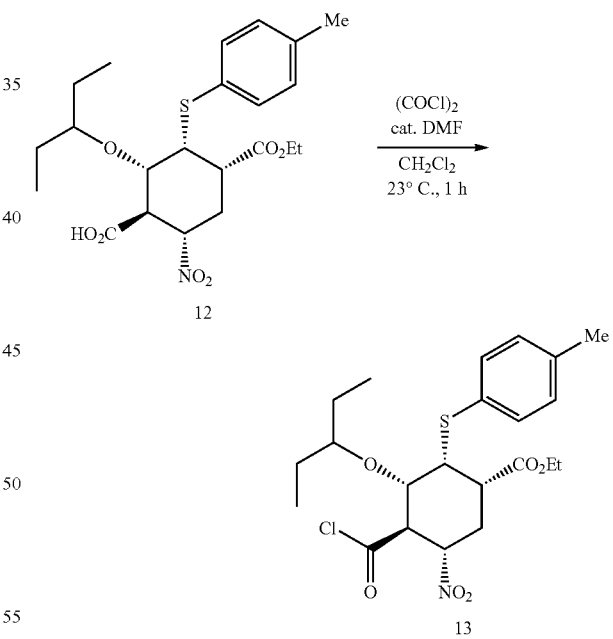

$^1$H NMR (400 MHz, CDCl$_3$) δ 7.39 (d, J=8.0 Hz, 2H), 7.08 (d, J=8.0 Hz, 2H), 4.70-4.80 (m, 1H), 4.10-4.20 (m, 1H), 4.03 (br s, 1H), 3.89-4.00 (m, 3H), 3.18 (quintet, J=4.4 Hz, 1H), 2.75 (dt, J=13.2, 3.2 Hz, 1H), 2.75 (dt, J=13.2, 4.0 Hz, 1H), 2.31 (s, 3H), 2.28 (q, J=13.2 Hz, 1H), 1.32-1.52 (m, 2H), 1.19 (t, J=7.2 Hz, 3H), 1.00-1.20 (m, 2H), 0.76 (t, J=7.2 Hz, 3H), 0.62 (t, J=7.2 Hz, 3H);

$^{13}$C NMR (100 MHz, CDCl$_3$) δ 172.8, 169.5, 137.9, 132.8 (2C), 130.5, 129.5 (2C), 82.6, 80.0, 76.5, 61.6, 58.7, 52.1, 43.2, 26.7, 24.6, 23.0, 21.0, 14.0, 8.6, 8.2;

IR (film) $v_{max}$ 2967, 1792, 1732, 1684, 1653, 1557, 1521, 1507, 1491, 1474, 1457, 1370, 1282, 1200, 1102, 1028, 950, 810 cm$^{-1}$;

HRMS (ESI) [M+Na]$^+$ calculated for [C$_{22}$H$_{30}$ClNNaO$_6$S]$^+$: 494.1375. found: 494.1381; $[\alpha]^{23}_D$ –18 (c 0.61, CHCl$_3$).

Reaction Example 20

Preparation of (1S,2R,3S,4R,5S)-Ethyl 4-(azidocarbonyl)-5-nitro-3-(3-pentanyloxy)-2-(p-tolylthio)cyclohexane Carboxylate (Compound 14)

To a solution of the compound 12 (40 mg, 0.088 mmol) in dichloromethane (1 mL) were added a catalytic amount of dimethyl formamide (2 µL) and oxalyl chloride (73 µL, 0.88 mmol) at 0° C. The resulting mixture was stirred for 1 hour at 23° C., and the solvent and excess oxalyl chloride were removed under reduced pressure. Saturated aqueous sodium azide (1 mL) was added to a solution of the crude material of the compound 13 in acetone (1 mL) at 0° C. The resulting mixture was stirred for 30 min at 0° C. before being quenched by addition of water. The aqueous layer was extracted three times with trichloromethane. The combined organic layer was washed with saturated aqueous sodium chloride, dried over magnesium sulfate, and concentrated under reduced pressure to give (1S,2R,3S,4R,5S)-ethyl 4-(azidocarbonyl)-5-nitro-3-(3-pentanyloxy)-2-(p-tolylthio)cyclohexane carboxylate (compound 14, 40.5 mg, yield 96%).

$^1$H NMR (400 MHz, CDCl$_3$) δ 7.38 (d, J=8.0 Hz, 2H), 7.07 (d, J=8.0 Hz, 2H), 4.66 (dt, J=4.8, 12.0 Hz, 1H), 4.07-4.18 (m, 1H), 4.00 (t, J=3.2 Hz, 1H), 3.85-3.97 (m, 1H), 3.78 (dd, J=10.8, 3.6 Hz, 1H), 3.47 (t, J=11.2 Hz, 1H), 3.13 (quintet, J=4.8 Hz, 1H), 2.76 (dt, J=13.2, 3.6 Hz, 1H), 2.68 (dt, J=13.2, 3.6 Hz, 1H), 2.31 (s, 3H), 2.28 (q, J=13.2 Hz, 1H), 1.28-1.48 (m, 2H), 1.21 (t, J=7.2 Hz, 3H), 1.03-1.18 (m, 2H), 0.76 (t, J=7.2 Hz, 3H), 0.63 (t, J=7.2 Hz, 3H);

$^{13}$C NMR (100 MHz, CDCl$_3$) δ 179.4, 169.7, 137.7, 132.9 (2C), 130.8, 129.6 (2C), 82.8, 80.4, 61.6, 52.5, 49.8, 43.4, 27.0, 24.8, 23.2, 21.0, 14.0, 8.9, 8.0 (1C overlapped CDCl$_3$);

IR (film) $v_{max}$ 2967, 2937, 2878, 2142, 1733, 1556, 1493, 1461, 1369, 1174, 1124, 1028, 810 cm$^{-1}$;

HRMS (ESI) [M+Na] calculated for [C$_{22}$H$_{30}$N$_4$NaO$_6$S]: 501.1778. found: 501.1776;

$[\alpha]^{23}_D$ –55 (c 1.01, CHCl$_3$).

Reaction Example 21

Preparation of (1S,2R,3S,4R,5S)-Ethyl 4-isocyanate-5-nitro-3-(3-pentanyloxy)-2-(p-tolylthio)cyclohexane Carboxylate (Compound 15)

A solution of the compound 14 (21 mg, 0.044 mmol) in benzene-d6 (0.5 mL) was put into an NMR sample tube for 36 hrs. After the solvent was removed, the compound 14 was completely converted to (1S,2R,3S,4R,5S)-ethyl 4-isocyanate-5-nitro-3-(3-pentanyloxy)-2-(p-tolylthio)cyclohexane carboxylate (compound 15, 20.5 mg, quantitative yield).

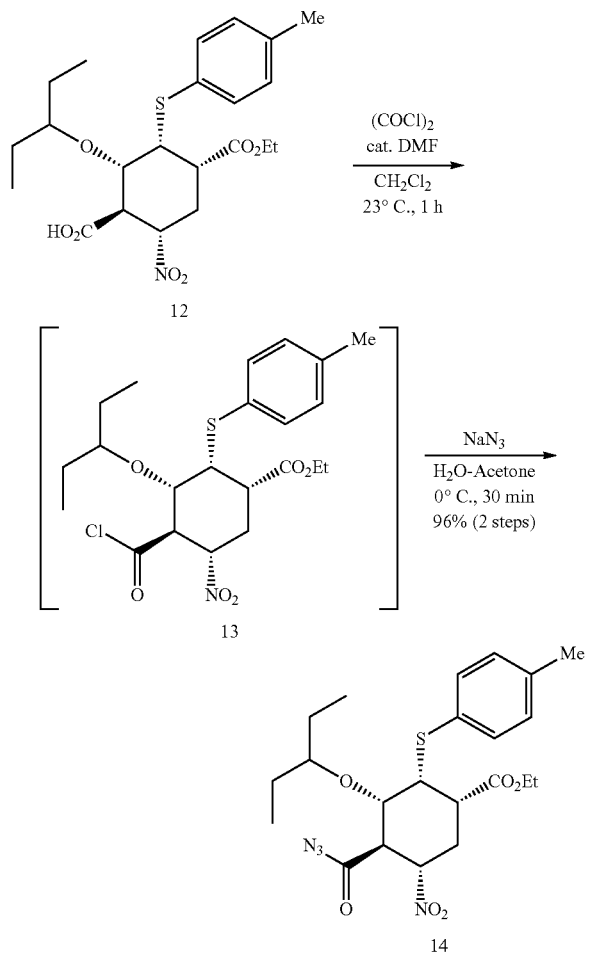

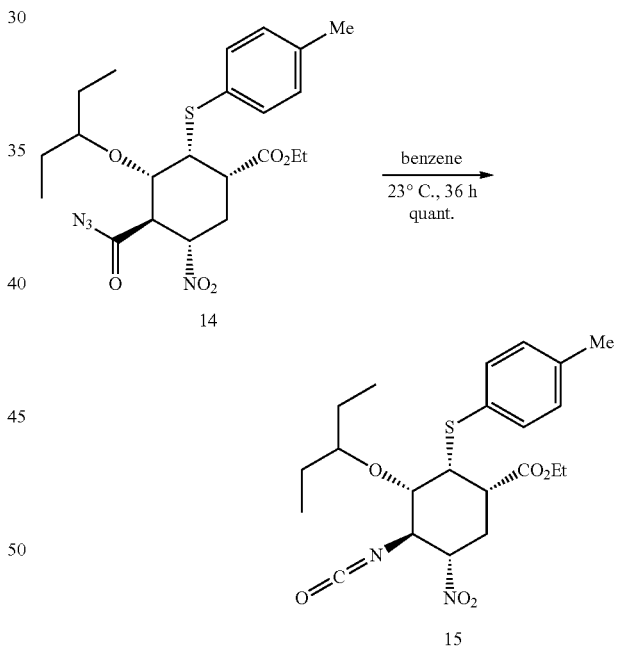

$^1$H NMR (400 MHz, C$_6$D$_6$) δ 7.47 (d, J=8.4 Hz, 2H), 6.81 (d, J=8.1 Hz, 2H), 4.57 (t, J=10.4 Hz, 1H), 3.89-4.00 (m, 2H), 3.80 (dt, J=4.4, 11.8 Hz, 1H), 3.67-3.75 (m, 1H), 3.01 (dd, J=10.0, 3.6 Hz, 1H), 2.97-3.05 (m, 2H), 2.37 (q, J=13.2 Hz, 1H), 2.08-2.17 (m, 1H), 1.98 (s, 3H), 1.92 (dt, J=13.2, 3.6 Hz, 1H), 1.40-1.50 (m, 1H), 1.28-1.38 (m, 1H), 1.00-1.20 (m, 1H), 0.90 (t, J=7.2 Hz, 3H), 0.74 (t, J=7.2 Hz, 3H), 0.61 (t, J=7.2 Hz, 3H);

$^{13}$C NMR (100 MHz, C$_6$D$_6$) δ 169.4, 137.7, 133.1 (2C), 131.8, 129.8 (2C), 86.6, 80.0, 77.5, 61.3, 57.1, 52.4, 43.2, 27.6, 25.2, 23.7, 20.8, 14.0, 8.8, 8.7 (O=C=N— undetected);

IR (film) $\nu_{max}$ 2968, 2938, 2878, 2245, 1736, 1559, 1493, 1456, 1369, 1251, 1201, 1100, 1029, 952, 862, 810 cm$^{-1}$;
HRMS (ESI) [M+Na]$^+$ calculated for [C$_{22}$H$_{30}$N$_2$NaO$_6$S]$^+$: 473.1717. found: 473.1719;
$[\alpha]^{23}{}_D$ –6.9 (c 1.41, CHCl$_3$).

Reaction Example 22

Preparation of (1S,2R,3S,4R,5S)-Ethyl 4-(N-acetylacetamide)-5-nitro-3-(3-pentanyloxy)-2-(p-tolylthio)cyclohexane Carboxyate (Compound 16)

Trifluoroacetic acid (1 mL) was added to a solution of the compound 7 (80 mg, 0.157 mmol) in dichloromethane (1 mL) at 23° C. under argon atmosphere. The reaction mixture was stirred for 4 hrs at 23° C. before removing the solvent and trifluoroacetic acid under reduced pressure. To a solution of the crude material of the compound 12 in dichloromethane (2 mL) were added a catalytic amount of dimethyl sulfoxide (one drop) and oxalyl chloride (150 µL, 1.57 mmol) at 0° C. The resulting mixture was stirred for 1 hour at 23° C. before removing the solvent and excess oxalyl chloride under reduced pressure. Saturated aqueous sodium azide (2 mL) was added to a solution of the crude material of the compound 13 in acetone (1 mL) at 0° C. The resulting mixture was stirred for 20 min at 0° C. before being quenched by addition of water. The aqueous layer was extracted three times with trichloromethane. The combined organic layer was washed with saturated aqueous sodium chloride, dried over magnesium sulfate to give the crude material of the compound 14. The crude material of the compound 14 was dissolved in acetic anhydride (2 mL), and the mixture was stirred for 36 hrs at 90° C. before removing the solvent under reduced pressure. The crude material was purified by flash column chromatography (solid phase: SiO$_2$, mobile phase: 10% ethyl acetate-n-hexane solution) to give (1S,2R,3S,4R,5S)-ethyl 4-(N-acetylacetamide)-5-nitro-3-(3-pentanyloxy)-2-(p-tolylthio)cyclohexane carboxylate (compound 16, 68.5 mg, yield 86%, 4step).

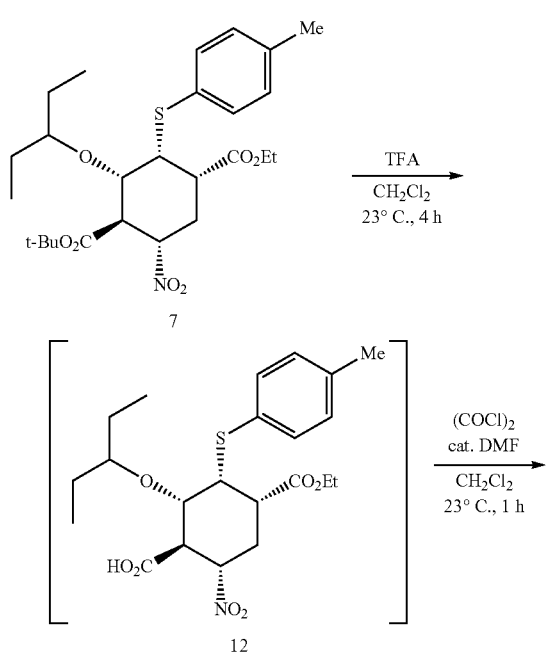

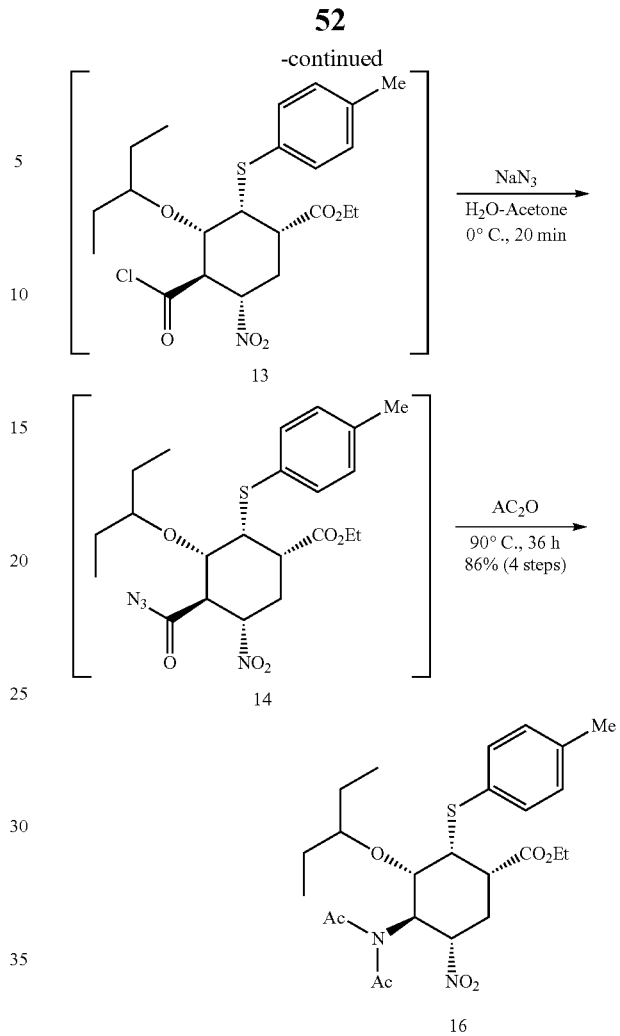

$^1$H NMR (400 MHz, CDCl$_2$) δ 7.38 (d, J=8.0 Hz, 2H), 7.08 (d, J=8.0 Hz, 2H), 5.52 (dt, J=4.8, 11.4 Hz, 1H), 4.71 (t, J=10.4 Hz, 1H), 4.43 (dd, J=10.0, 3.6 Hz, 1H), 4.12-4.20 (m, 1H), 4.09 (br s, 1H), 3.93-4.03 (m, 1H), 3.06 (quintet, J=4.2 Hz, 1H), 2.87 (dt, J=10.0, 3.2 Hz, 1H), 2.55-2.65 (m, 1H), 2.50 (s, 3H), 2.42 (q, J=13.2 Hz, 1H), 2.40 (s, 3H), 2.31 (s, 3H), 1.22-1.32 (m, 2H), 1.22 (t, J=7.2 Hz, 3H), 0.90-1.10 (m, 2H), 0.66 (t, J=7.2 Hz, 3H), 0.55 (t, J=7.2 Hz, 3H);
$^{13}$C NMR (100 MHz, CDCl$_3$) δ 176.0, 174.5, 169.8, 137.7, 132.7 (2C), 131.0, 129.6 (2C), 81.7, 80.1, 74.0, 61.6, 59.8, 54.1, 42.9, 28.5, 28.3, 25.0, 24.3, 23.2, 21.0, 14.1, 8.4, 8.2;
IR (film) $\nu_{max}$ 2966, 2933, 2880, 1721, 1701, 1556, 1493, 1457, 1368, 1278, 1253, 1229, 1191, 1095, 1030, 971, 810 cm$^{-1}$;
HRMS (ESI) [M+Na]$^+$ calculated for [C$_{25}$H$_{36}$N$_2$NaO$_7$S]$^+$: 531.2135. found: 531.2136;
$[\alpha]^{23}{}_D$ –22 (c 0.59, CHCl$_3$).

Reaction Example 23

Preparation of (1S,2R,3S,4R,5S)-Ethyl 4-acetamide-5-nitro-3-(3-pentanyloxy)-2-(p-tolylthio)cyclohexane Carboxylate (Compound 17)

Hydrazine monohydrate (7.2 µL, 0.299 mmol) was added to a solution of the compound 16 (15.2 mg, 0.03 mmol) in ethanol (0.5 mL) at 23° C. under argon atmosphere. The reaction mixture was stirred for 3 hrs at 23° C. before removing the solvent under reduced pressure. When the crude material formed crystals, they were washed with a 20% ethyl acetate-n-hexane solution to provide (1S,2R,3S,4R,5S)-ethyl 4-acetamide-5-nitro-3-(3-pentanyloxy)-2-(p-tolylthio)cyclohexane carboxylate (compound 17, 10.8 mg, yield 78%).

rated aqueous sodium chloride, dried over magnesium sulfate, and concentrated under reduced pressure. Preparative thin layer chromatography (solid phase: $SiO_2$, mobile phase: 20% methanol-trichloromethane solution) provided (1S,2R,3S,4R,5S)-ethyl 4-acetamide-5-amino-3-(3-pentanyloxy)-2-(p-tolylthio)cyclohexane carboxylate (compound 18, 24 mg, yield 86%).

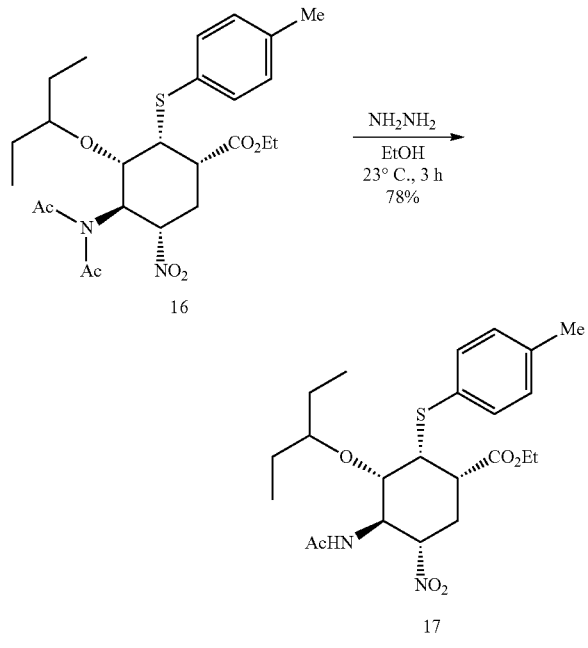

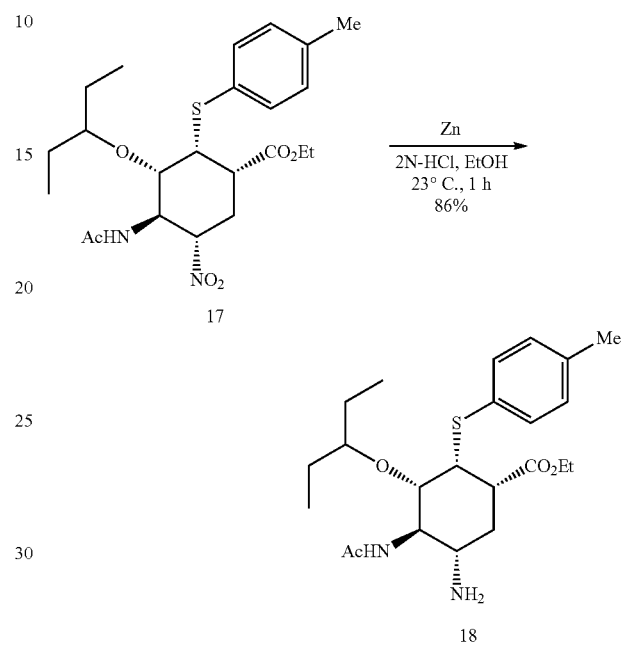

mp 192-195° C.;

$^1$H NMR (400 MHz, $CDCl_3$) δ 7.37 (d, J=8.0 Hz, 2H), 7.05 (d, J=8.0 Hz, 2H), 5.88 (d, J=6.4 Hz, 1H), 5.50 (dt, J=4.8, 12.0 Hz, 1H), 4.42 (dd, J=4.0, 10.4 Hz, 1H), 4.08-4.14 (m, 1H), 4.05-4.06 (m, 1H), 3.84-3.94 (m, 2H), 3.15-3.21 (m, 1H), 2.87 (td, J=2.8, 13.2 Hz, 1H), 2.52-2.55 (m, 1H), 2.35 (q, J=12.8 Hz, 1H), 2.30 (s, 3H), 1.93 (s, 3H), 1.31-1.50 (m, 2H), 1.17 (t, J=7.0 Hz, 3H), 1.05-1.14 (m, 2H), 0.81 (t, J=7.4 Hz, 3H), 0.61 (t, J=7.4 Hz, 3H);

$^{13}$C NMR (100 MHz, $CDCl_3$) δ 171.4, 170.0, 137.4, 132.7 (2C), 131.4, 129.5 (2C), 82.8, 80.8, 73.4, 61.3, 55.6, 54.1, 43.0, 27.9, 25.2, 24.1, 23.7, 20.9, 13.9, 9.0, 8.8;

IR (film) $v_{max}$ 3274, 2965, 2878, 1738, 1660, 1556, 1494, 1455, 1370, 1199, 1098, 1031, 947, 863, 810, 737, 606 $cm^{-1}$;

HRMS (ESI) $[M+Na]^+$ calculated for $[C_{23}H_{34}N_2NaO_6S]^+$: 489.2030. found: 489.2020;

$[α]^{23}_D$ –41 (c 0.32, $CHCl_3$).

Reaction Example 24

Preparation of (1S,2R,3S,4R,5S)-Ethyl 4-acetamide-5-amino-3-(3-pentanyloxy)-2-(p-tolylthio)cyclohexane Carboxylate (Compound 18)

Activated zinc powder (630 mg, washed with 1 N hydrochloric acid, water, ethanol and diethyl ether before use) was added to a solution of the compound 17 (30 mg, 0.064 mmol) in ethanol (1 mL) and 2 N hydrochloric acid (1 mL) at 23° C. under argon atmosphere. The reaction mixture was stirred for 3 hrs at 23° C. before filtration. To the filtrate was added 28% ammonium hydroxide in water. The aqueous layer was extracted three times with a 10% methanol-trichloromethane solution. The combined organic layer was washed with satu- $^1$H NMR (400 MHz, $CDCl_3$) δ 7.36 (d, J=8.0 Hz, 2H), 7.02 (d, J=8.0 Hz, 2H), 6.20 (br s, 1H), 4.00-4.10 (m, 1H), 4.00 (br s, 1H), 3.82-3.90 (m, 2H), 3.60-3.70 (m, 1H), 3.22-3.32 (m, 1H), 3.20 (quinted, J=4.2 Hz, 1H), 2.81 (dt, J=12.8, 2.8 Hz, 1H), 2.50-2.80 (m, 2H), 2.28 (s, 3H), 2.21 (br d, J=14.0 Hz, 1H), 2.04 (s, 3H), 1.84 (q, J=12.8 Hz, 1H), 1.32-1.50 (m, 2H), 1.05-1.20 (m, 2H), 1.14 (t, J=7.0 Hz, 3H), 0.82 (t, J=7.4 Hz, 3H), 0.62 (t, J=7.4 Hz, 3H);

$^{13}$C NMR (100 MHz, $CDCl_3$) δ 171.6, 171.3, 136.9, 132.6 (2C), 132.3, 129.4 (2C), 80.5, 76.4, 60.9, 54.5, 50.8, 43.9, 29.7 (br), 29.3 (br), 25.1, 24.1 (2C), 21.0, 14.0, 9.1, 8.7;

IR (film) $v_{max}$ 3446, 2962, 2932, 2875, 1733, 1653, 1558, 1493, 1457, 1373, 1300, 1194, 1112, 1032, 947, 810 $cm^{-1}$;

HRMS (ESI) $[M+Na]^+$ calculated for $[C_{23}H_{36}N_2NaO_4S]^+$: 459.2288. found: 459.2293;

$[α]^{20}_D$ –18 (c 0.49, $CHCl_3$).

Reaction Example 25

Preparation of (–)-Oseltamivir

Potassium carbonate (195.4 mg, 1.4 mmol) was added to a solution of the compound 18 (8.8 mg, 0.02 mmol) in ethanol (2 mL) at 23° C. The reaction mixture was stirred for 4 hrs before filtration. After removing excess ethanol under reduced pressure, 2 N hydrochloric acid was added to the residue at 0° C. The aqueous layer was washed with ethyl acetate followed by adjustment to pH of 11 with 28% ammonium hydroxide in water. The aqueous layer was extracted three times with 10% methanol-trichloromethane. The combined organic layer was washed with saturated aqueous sodium chloride, dried over magnesium sulfate, and concentrated under reduced pressure to afford (−)-oseltamivir (compound 1, 5.7 mg, yield 91%). All spectral data were identical with reported data.

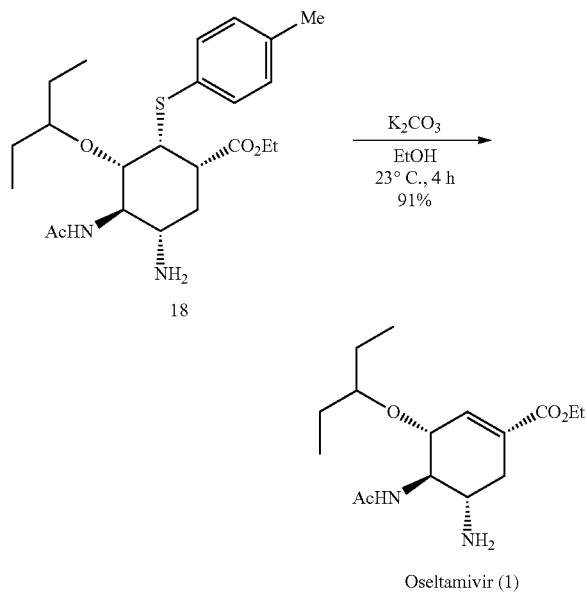

$^1$H NMR (400 MHz, CDCl$_3$) δ 6.78 (t, J=2.0 Hz, 1H), 5.62 (d, J=7.6 Hz, 1H), 4.20 (q, J=7.2 Hz, 2H), 4.15-4.20 (m, 1H), 3.52 (q, J=8.0 Hz, 1H), 3.34 (quintet, J=5.6 Hz, 1H), 3.24 (dt, J=5.2, 10.0 Hz, 1H), 2.75 (dd, J=17.6, 5.2 Hz, 1H), 2.15 (ddt, J=17.6, 10.0, 2.8 Hz, 1H), 2.04 (s, 3H), 1.40-1.60 (m, 4H), 1.29 (t, J=7.2 Hz, 3H), 0.90 (t, J=7.2 Hz, 3H), 0.89 (t, J=7.2 Hz, 3H), —NH$_2$ undetected;

$^{13}$C NMR (100 MHz, CDCl$_3$) δ 170.9, 166.3, 137.5, 129.6, 81.7, 74.8, 60.8, 59.0, 49.2, 33.6, 26.3, 25.8, 23.7, 14.2, 9.5, 9.3;

IR (film) ν$_{max}$ 3276, 3077, 2965, 2936, 2877, 1715, 1655, 1558, 1464, 1374, 1303, 1244, 1195, 1127, 1064, 1031, 944, 861, 778, 736 cm$^{-1}$;

HRMS (ESI) [M+Na]$^+$ calculated for [C$_{16}$H$_{28}$N$_2$NaO$_4$]+: 335.1941. found: 335.1934;

[α]$^{23}_D$ −54.9 (c 0.68, CHCl$_3$).

Reaction Example 26

One-pot Reaction from Compound 7 to Give (−)-Oseltamivir

Trifluoroacetic acid (0.5 mL) was added to a solution of the compound 7 (215 mg, 0.422 mmol) in dichloromethane (1 mL) at 23° C. under argon atmosphere. The reaction mixture was stirred for 2 hrs at 23° C. before removing the solvent and trifluoroacetic acid under reduced pressure. To a solution of the resulting compound 12 in dichloromethane (1.5 mL) were added a catalytic amount of dimethyl formamide (one drop) and oxalyl chloride (357 μL, 4.22 mmol) at 0° C. The resulting reaction mixture was stirred for 1 hour at 23° C. before removing the solvent and excess oxalyl chloride under reduced pressure. Saturated aqueous sodium azide (0.5 mL) was added to a solution of the crude material of the resulting compound 13 in acetone (1 mL) at 0° C. The resulting reaction mixture was stirred for 20 min at 0° C. before being quenched by addition of water. The aqueous layer was extracted three times with trichloromethane. The combined organic layer was washed with saturated aqueous sodium chloride, dried over magnesium sulfate, and concentrated under reduced pressure to give the crude material of the compound 14. The crude material of the compound 14 was dissolved in acetic anhydride (2 mL), and the reaction mixture was stirred for 36 hrs at 90° C. before removing the solvent under reduced pressure. To a solution of the crude material of the compound 16 in ethanol (3 mL) was added hydrazine monohydrate (40.9 μL, 0.844 mmol) at 23° C. under argon atmosphere. The resulting reaction mixture was stirred for 2 hrs at 23° C. before removing the solvent under reduced pressure. Activated Zn powder (1.38 g, 21.1 mmol, washed with 1 N hydrochloric acid, water, ethanol, and diethyl ether before use) was added to a solution of the crude material of the resulting compound 17 in ethanol (4 mL) and trimethyl chlorosilane (1.62 mL, 12.7 mmol) at 23° C. under argon atmosphere. The reaction mixture was stirred for 1 hour at 70° C. before bubbling ammonia gas for 10 min at 0° C. To the resulting reaction mixture was added potassium carbonate (1.17 g, 8.44 mmol) at 23° C. and stirred for 6 hrs at 23° C. before filtration. After removing excess ethanol under reduced pressure, 2 N hydrochloric acid was added to the residue at 0° C. The aqueous layer was washed with ethyl acetate followed by adjustment to pH of 11 with 28% ammonium hydroxide in water. The aqueous layer was extracted three times with 10% methanol-trichloromethane. The combined organic layer was washed with saturated aqueous sodium chloride, dried over magnesium sulfate, and concentrated under reduced pressure to afford (−)-oseltamivir (compound 1, 109.5 mg, yield 83% calculated from the compound 8 as a standard).

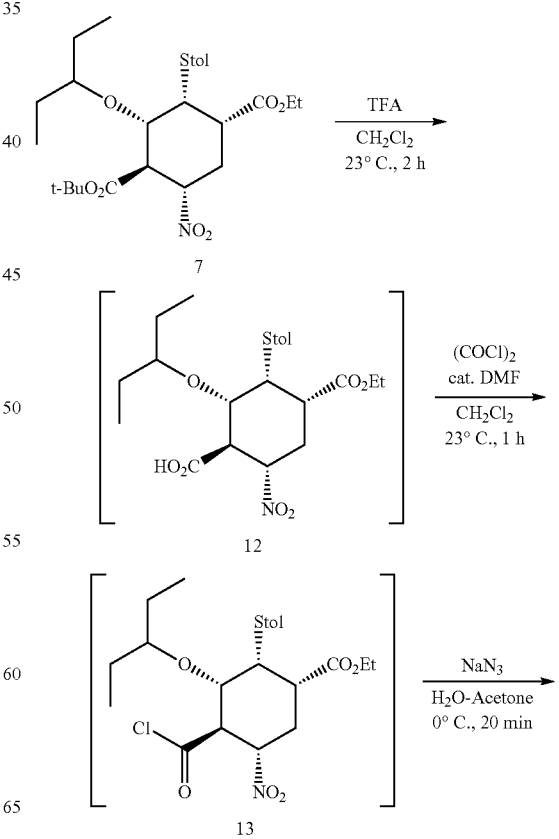

-continued

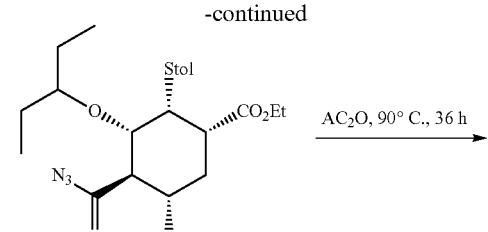

14

AC₂O, 90° C., 36 h

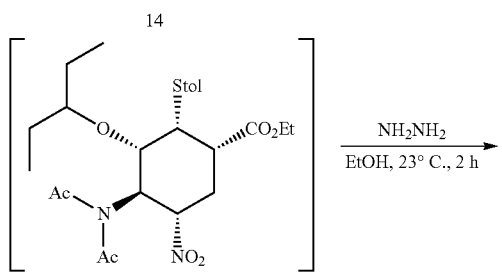

16

NH₂NH₂
EtOH, 23° C., 2 h

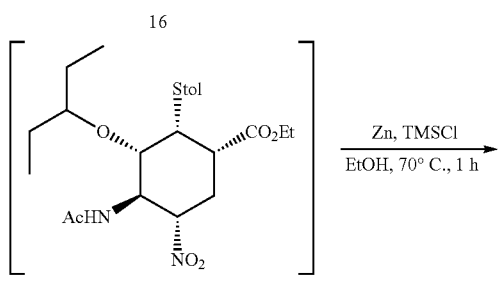

17

Zn, TMSCl
EtOH, 70° C., 1 h

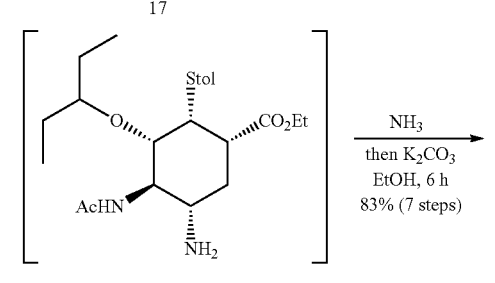

18

NH₃
then K₂CO₃
EtOH, 6 h
83% (7 steps)

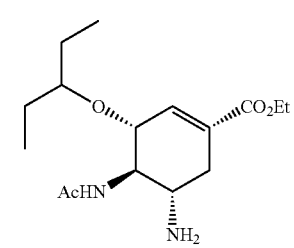

(-)-Oseltamivir (1)

The invention claimed is:

1. A process for producing oseltamivir phosphate comprising the following steps (1-1) to (1-8):

(1-1) subjecting a compound represented by the following general formula (I) and a compound represented by the following general formula (II) to a Michael reaction, and subjecting thus obtained compound and a compound represented by the following general formula (III) or the general formula (IV) to a Michael reaction and a Horner-Wadsworth-Emmons reaction to obtain a compound represented by the following general formula (V):

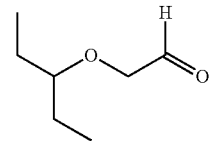

(I)

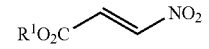

(II)

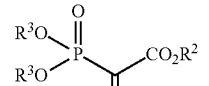

(III)

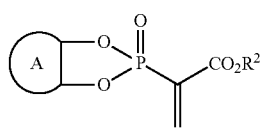

(IV)

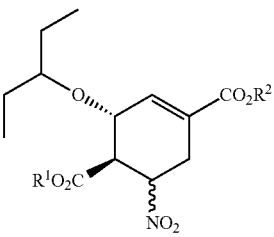

(V)

wherein, $R^1$ represents a protecting group of a carboxyl group; $R^2$ represents an alkyl group, an aryl group, a heteroaryl group, a cycloalkyl group, or a heterocycloalkyl group which may have a substituent; $R^3$ each independently represents an alkyl group, an aryl group, a heteroaryl group, a cycloalkyl, group, or a heterocycloalkyl group which may have a substituent, and may form a ring structure by linking with each other; and A represents an arylene group, a heteroarylene group, a cycloalkylene group, or a heterocycloalkylene group which may have a substituent;

(1-2) subjecting the compound represented by the above general formula (V) and a thiol compound to a Michael reaction to obtain a compound represented by the following general formula (VI):

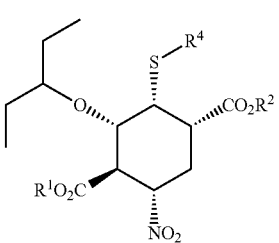

(VI)

wherein, $R^1$ and $R^2$ are as defined above; and $R^4$ represents an aryl group, a heteroaryl group, a cycloalkyl group, a heterocycloalkyl group, a cycloalkenyl group, a heterocycloalkenyl group, an alkyl group, an alkenyl group, or an alkynyl group which may have a substituent;

(1-3) reducing the compound represented by the above general formula (VI), and subjecting to a reverse Michael reaction to obtain a compound represented by the following general formula (VII):

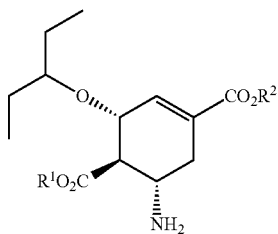
(VII)

wherein, $R^1$ and $R^2$ are as defined above;

(1-4) protecting an amino group of the compound represented by the above general formula (VII) and deprotecting a carboxyl group to obtain a compound represented by the following general formula (VIII):

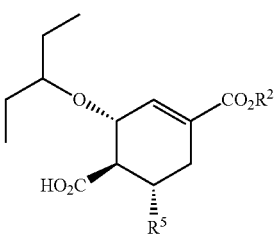
(VIII)

wherein, $R^2$ is as defined above; and $R^5$ represents a group in which a protecting group is bound to an amino group;

(1-5) halogenating a carboxyl group of the compound represented by the above general formula (VIII) to obtain a compound represented by the following general formula (IX):

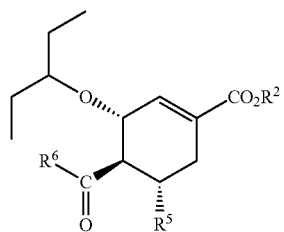
(IX)

wherein, $R^2$ and $R^5$ are as defined above; and $R^6$ represents a halogen atom;

(1-6) allowing the compound represented by the above general formula (IX) to react with an azide to obtain a compound represented by the following general formula (X):

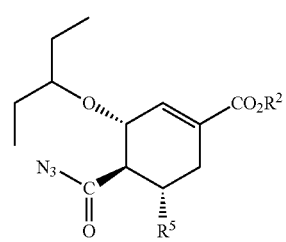
(X)

wherein, $R^2$ and $R^5$ are as defined above;

(1-7) subjecting the compound represented by the above general formula (X) to a Curtius rearrangement reaction to obtain a compound represented by the following general formula (XI):

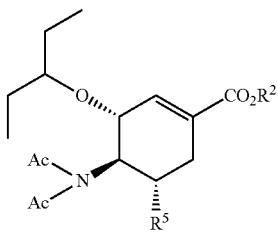
(XI)

wherein, $R^2$ and $R^5$ are as defined above; and (1-8) deacetylating the compound represented by the above general formula (XI) and deprotecting an amino group to obtain a compound represented by the following general formula (XII):

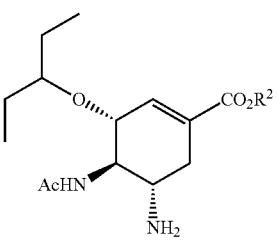
(XII)

wherein, $R^2$ is as defined above.

2. A process for producing oseltamivir phosphate comprising the following steps (2-1) to (2-9):

(2-1) subjecting a compound represented by the following general formula (I) and a compound represented by the following general formula (II) to a Michael reaction, and subjecting thus obtained compound and a compound represented by the following general formula (III) or the general formula (IV) to a Michael reaction and a Horner-Wadsworth-Emmons reaction to obtain a compound represented by the following general formula (V):

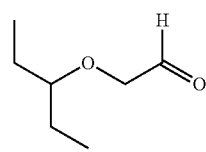
(I)

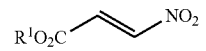
(II)

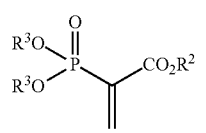
(III)

-continued

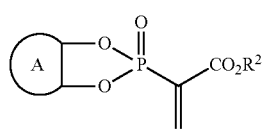
(IV)

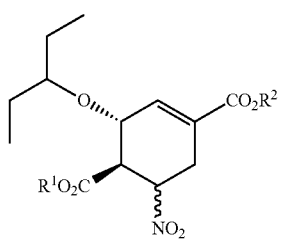
(V)

wherein, $R^1$ represents a protecting group of a carboxyl group; $R^2$ represents an alkyl group, an aryl group, a heteroaryl group, a cycloalkyl group, or a heterocycloalkyl group which may have a substituent; $R^3$ each independently represents an alkyl group, an aryl group, a heteroaryl group, a cycloalkyl group, or a heterocycloalkyl group which may have a substituent, and may form a ring structure by linking with each other; and A represents an arylene group, a heteroarylene group, a cycloalkylene group, or a heterocycloalkylene group which may have a substituent;

(2-2) subjecting the compound represented by the above general formula (V) and a thiol compound to a Michael reaction to obtain a compound represented by the following general formula (VI):

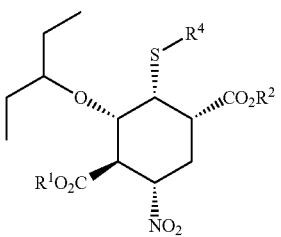
(VI)

wherein, $R^1$ and $R^2$ are as defined above; and $R^4$ represents an aryl group, a heteroaryl group, a cycloalkyl group, a heterocycloalkyl group, a cycloalkenyl group, a heterocycloalkenyl group, an alkyl group, an alkenyl group, or an alkynyl group which may have a substituent;

(2-3) deprotecting a carboxyl group of the compound represented by the above general formula (VI) to obtain a compound represented by the following general formula (XIII):

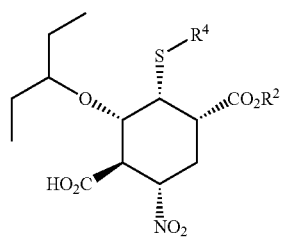
(XIII)

wherein, $R^2$ and $R^4$ are as defined above;

(2-4) halogenating a carboxyl group of the compound represented by the above general formula (XIII) to obtain a compound represented by the following general formula (XIV):

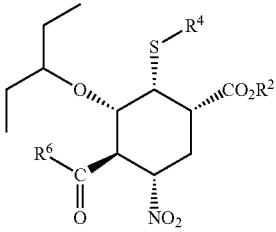
(XIV)

wherein, $R^2$ and $R^4$ are as defined above; and $R^6$ represents a halogen atom:

(2-5) allowing the compound represented by the above general formula (XIV) to react with an azide to obtain a compound represented by the following general formula (XV):

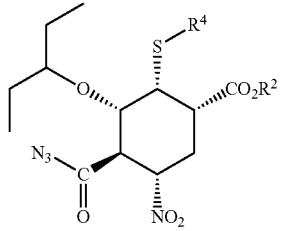
(XV)

wherein, $R^2$ and $R^4$ are as defined above;

(2-6) subjecting the compound represented by the above general formula (XV) to a Curtius rearrangement reaction to obtain a compound represented by the following general formula (XVI):

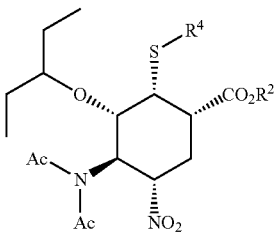
(XVI)

wherein, $R^2$ and $R^4$ are as defined above;

(2-7) deacetylating the compound represented by the above general formula (XVI) to obtain a compound represented by the following general formula (XVII):

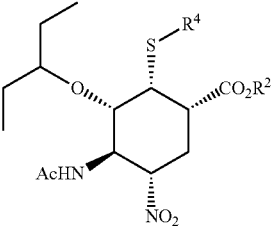
(XVII)

wherein, $R^2$ and $R^4$ are as defined above;

(2-8) reducing the compound represented by the above general formula (XVII) to obtain a compound represented by the following general formula (XVIII):

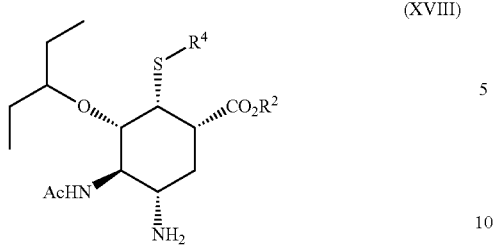
(XVIII)
wherein, $R^2$ and $R^4$ are as defined above; and
(2-9) subjecting the compound represented by the above general formula (XVIII) to a reverse Michael reaction to obtain a compound represented by the following general formula (XII):
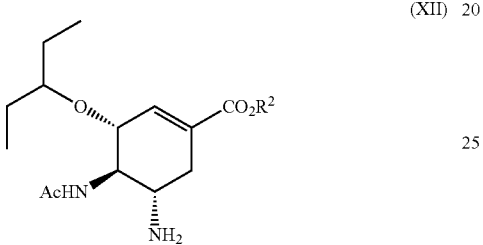
(XII)
wherein, $R^2$ is as defined above.
* * * * *